United States Patent
Czabany et al.

(10) Patent No.: US 9,481,902 B2
(45) Date of Patent: Nov. 1, 2016

(54) QUANTITATIVE CONTROL OF SIALYLATION AND SPECIFIC MONO-SIALYLATION

(71) Applicant: Roche Diagnostics Operations, Inc., Indianapolis, IN (US)

(72) Inventors: Tibor Czabany, Graz (AT); Alfred Engel, Weilheim (DE); Michael Greif, Penzberg (DE); Christine Jung, Iffeldorf (DE); Christiane Luley, Hoef-Praebach (AT); Sebastian Malik, Antdorf (DE); Rainer Mueller, Penzberg (DE); Bernd Nidetzky, Graz (AT); Doris Ribitsch, Graz (AT); Katharina Schmoelzer, Graz (AT); Helmut Schwab, Graz (AT); Harald Sobek, Biberach (DE); Bernhard Suppmann, Weilheim (DE); Marco Thomann, Penzberg (DE); Sabine Zitzenbacher, Graz (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/970,734

(22) Filed: Dec. 16, 2015

(65) Prior Publication Data

US 2016/0102333 A1  Apr. 14, 2016

Related U.S. Application Data

(63) Continuation of application No. PCT/EP2014/064213, filed on Jul. 3, 2014.

(30) Foreign Application Priority Data

Jul. 5, 2013  (EP) ..................................... 13175347

(51) Int. Cl.
| | | |
|---|---|---|
| *C07K 16/00* | (2006.01) | |
| *C12Q 1/00* | (2006.01) | |
| *C12P 21/00* | (2006.01) | |
| *C12N 9/10* | (2006.01) | |

(52) U.S. Cl.
CPC ............... *C12P 21/005* (2013.01); *C07K 16/00* (2013.01); *C12N 9/1081* (2013.01); *C07K 2317/14* (2013.01); *C07K 2317/24* (2013.01); *C07K 2317/41* (2013.01); *C12Y 204/99001* (2013.01)

(58) Field of Classification Search
None
See application file for complete search history.

(56) References Cited

U.S. PATENT DOCUMENTS

| 5,032,519 A | 7/1991 | Paulson et al. |
| 2013/0071390 A1 | 3/2013 | Stadheim et al. |

FOREIGN PATENT DOCUMENTS

| WO | 2005/023872 A1 | 3/2005 |
| WO | WO2005076013 | * 8/2005 |
| WO | 2007/135194 A2 | 11/2007 |
| WO | 2012/113863 A1 | 8/2012 |

OTHER PUBLICATIONS

Altschul, Stephen F. et al., Gapped BLAST and PSI-BLAST: a new generation of protein database search programs, Nucleic Acids Research, 1997, pp. 3389-3402, vol. 25, No. 17.
Anderson, J. Christopher et al., An expanded genetic code with a functional quadruplet codon, Proceedings of the National Academy of Sciences USA, 2004, pp. 7566-7571, vol. 101, No. 20.
Bacher, Jamie M. and Ellington, Andrew D., Selection and Characterization of *Escherichia coli* Variants Capable of Growth on an Otherwise Toxic Trytophan Analogue, Journal of Bacteriology, 2001, pp. 5414-5425, vol. 183, No. 18.
Backliwal, Gaurav et al., Rational vector design and multi-pathway modulation of HEK 293E cells yield recombinant antibody tiers exceeding 1 g/l by transient transfaction under serum-free conditions, Nucleic Acids Research, 2008, 2.96, 7 pages, vol. 36, No. 15.
Barb, Adam W., et al., Branch-Specific Sialylation of IgG-Fc Glycans by ST6Gal-I, Biochemistry, 2009, pp. 9705-9707, vol. 48.
Bork, Kaya et al., Increasing the Sialylation of Therapeutic Glycoproteins: The Potential of the Sialic Acid Biosynthetic Pathway, Journal of Pharmaceutical Sciences, 2009, pp. 3499-3508, vol. 98, No. 10.
Brossmer, Reinhard and Gross, Hans Jürgen, [12] Flourescent and Photoactivatable Sialic Acids, Methods in Enzymology, 1994, pp. 177-183, vol. 247.

(Continued)

*Primary Examiner* — Suzanne M Noakes
*Assistant Examiner* — Jae W Lee
(74) *Attorney, Agent, or Firm* — Roche Diagnostics Operation, Inc.

(57) ABSTRACT

The present disclosure is directed to the use of certain glycosyltransferase variants having N-terminal truncation deletions. It was found that the combination of two different truncation variants of human β-galactoside-α-2,6-sialyltransferase I (hST6Gal-I) exhibited different specific sialyltransferase enzymatic activities. In one example, under conditions wherein the first variant Δ89 hST6Gal-I catalyzed formation of bi-sialylated target molecules the second variant Δ108 hST6Gal-I catalyzed formation of mono-sialylated target molecules. Thus, disclosed are variants of mammalian glycosyltransferase, nucleic acids encoding the same, methods and means for recombinantly producing the variants of mammalian glycosyltransferase and use thereof, particularly for sialylating in a quantitatively controlled manner terminal acceptor groups of glycan moieties being part of glycoproteins such as immunoglobulins.

12 Claims, 3 Drawing Sheets

(56) References Cited

OTHER PUBLICATIONS

Budisa, Nediljko et al., Proteins with β-(thienophnrolyl)alanines as alternative chromophores and pharmaceutically active amino acids, Protein Science, 2001, pp. 1281-1292, vol. 10.

Chen, Chun and Colley, Karen J., Minimal structural and glycosylation requirements for ST6Gal I activity and trafficking, Glycobiology, 2000, pp. 531-583, vol. 10, No. 5.

Chin, Jason W. et al., An Expanded Eukaryotic Genetic Code, Science, 2003, pp. 964-967, vol. 301.

Chung, Seung-Wook et al., Galactosylation and sialylation of terminal glycan residues of human immunoglobulin G using bacterial glycosyltransferases with in situ regeneration of sugar-nucleotides, Enzyme and Microbial Technology, 2006, pp. 60-66, vol. 39, No. 1.

Dall'olio, Fabio, The sialyl-α2, 6-lactosaminyl-structure: Biosynthesis and functional role, Glycoconjugate Journal, 2000, pp. 669-676, vol. 17.

Donadio, Sandrine et al., Recognition of cell surface acceptors by two human α-2,6-sialyltransferases produced in CHO cells, Biochimie, 2003, pp. 311-321, vol. 85.

Engel, Alfred M. et al, Rec. ST6Gal-I variants to control enzymatic activity in processes of in vitro glycoengineering, BMC Proceedings, 2013, pp. P110-P111, vol. 7 (Supplement 6).

Hamano-Takaku, Fumie et al., A Mutant *Escherichia coli* Tyrosyl-tRNA Synthetase Utilizes the Unnatural Amino Acid Azatyrosine More Efficiently than Tyrosine, The Journal Biological Chemistry, 2000, pp. 40324-40328, vol. 275, No. 51.

Hidari, Kazuya I.P.J. et al., Purification and characterization of a soluble recombinant human ST6Gal I functionally expressed in *Escherichia coil*, Glycoconjugate Journal, 2005, pp. 1-11, vol. 22.

IBBA, Michael and Söll, Dieter, Genetic Code: Introducing Pyrrolysine, Current Biology, 2002, pp. R464-R466, vol. 12.

Ikeda, Yutaka et al., Synthesis of a novel histidine analogue and its efficient incorporation into a protein in vivo, Protein Engineering, 2003, pp. 699-706, vol. 16, No. 9.

International Search Report issued Nov. 6, 2014 in Application No. PCT/EP2014/064213, 8 pages.

James, D. Andrew et al., Kinetic characterization of ribonuclease S mutants containing photoisomerizable phenylazophenylalanine residues, Protein Engineering, 2001, pp. 983-991, vol. 14, No. 12.

Kilar, Ferenc and Hjertén, Stellan, Separation of the Human Transferrin Isoforms by Carrier-Free High-Performance Zone Electrophoresis and Isoelectric Focusing, Journal of Chromatography, 1989, pp. 351-357, vol. 480.

Kitazume-Kawaguchi, Shinobu et al., The relationship between ST6Gal I Golgi retention and its cleavage-secretion, Glycobiology, 1999, pp. 1397-1406, vol. 9, No. 12.

Köhrer, Caroline et al., Import of amber and ochre suppressor tRNAs into mammalian cells: A general approach to site-specific insertion of amino acid analogues into proteins, Proceedings of the National Academy of Sciences USA, 2001, pp. 14310-14315, vol. 98, No. 25.

Legaigneur, Patrick et al., Exploring the Acceptor Substrate Recognition of the Human β-Galactoside α2,6-Sialyltransferase, The Journal of Biological Chemistry, 2000, pp. 21608-21617, vol. 276, No. 24.

Lund, John et al., Control of IgG/Fc Glycosylation: A Comparison of Oligosaccharides from Chimeric Human/Mouse and Mouse Subclass Immunoglobulin Gs, Molecular Immunology, 1993, pp. 741-748, vol. 30, No. 8.

Malissard, M. et al., Expression of Functional Soluble Forms of Human β-1,4-Galactosyltransferase I, α-2,6-Sialyltransferase, and a α-1,3-Fucosyltransferase VI in the Methylotrophic Yeast Pichia pastoris, Biochemical and Biophysical Research Communications, 2000, pp. 169-173, vol. 267.

Nakamura, Mitsuru et al., CMP-NeuAc:Galβ1→4GlcNAc α2→6sialyltransferase catalyzes NeuAc transfer to glycoplipids, Journal of Lipid Research, 1997, pp. 1795-1806, vol. 38.

Nielsen, Peter E. et al., Sequence-Selective Recognition of DNA by Strand Displacement with a Thymine-Substituted Polyamide, Science, 1991, pp. 1497-1500, vol. 254.

Ogata, Makoto et al., Synthesis of sialoglycopolypeptide for potentially blocking influenza virus infection using a rat α2,6-sialyltransferase expressed in BmNPV bacmid-injected silkworm larvae, BMC Biotechnology, 2009, 54, 13 pages, vol. 9.

Stadtman, Thressa C., Selenocysteine, Annual Reviews of Biochemistry, 1996, pp. 83-100, vol. 65.

Zhang, Zhiwen et al., Selective incorporation of 5-hydroxytryptophan into proteins in mammalian cells, Proceedings of the National Academy of Sciences USA, 2004, pp. 8882-8887, vol. 101, No. 24.

Anumula, Kalyan Rao, Quantitative glycan profiling of normal human plasma derived immunoglobulin and its fragments Fab and FC, Journal of Immunological Methods, 2012, pp. 167-176, vol. 382.

Hamako, Jiharu et al., Comparative Studies of Asparagine-Linked Sugar Chains of Immunoglobulin G from Eleven Mammalian Species, Comparative Biochemistry and Physiology Part B, 1993, pp. 949-954, vol. 106B, No. 4.

Nikonova, E. Yu et al., Specificity of human trans-sialidase as probed with gangliosides, Bioorganic & Medicinal chemistry Letters, 2004, pp. 5161-5164, vol. 14.

Patel, Ronak Y. and Balaji, Petery V., Identification of linkage-specific sequence motifs in sialyltransferases, Glycobiology, 2006, pp. 108-116, vol. 16, No. 2.

Scudder, Peter R. and Chantler, Eric N., Glycosyltransferases of the Human Cervical Epithelium II. Characterization of a CMP-N-Acetylneuraminate: Galactosyl-Glycoprotein Sialyltransferase, Biochimica et Biophysica Acta, 1981, pp. 136-141, vol. 660.

Sticher, Udo et al., Purification and characterization of α(2-6)-sialyltransferase from human liver, Glycoconjugate Journal, 1991, pp. 45-54, vol. 8.

\* cited by examiner

SEQUENCE LISTING

<160> NUMBER OF SEQ ID NOS: 7

<210> SEQ ID NO 1
<211> LENGTH: 406

```
<212> TYPE: PRT
<213> ORGANISM: Homo sapiens
<220> FEATURE:
<221> NAME/KEY: MISC_FEATURE
<223> OTHER INFORMATION: hST6-Gal-I WT polypeptide

<400> SEQUENCE: 1

Met Ile His Thr Asn Leu Lys Lys Lys Phe Ser Cys Cys Val Leu Val
1               5                   10                  15

Phe Leu Leu Phe Ala Val Ile Cys Val Trp Lys Glu Lys Lys Lys Gly
            20                  25                  30

Ser Tyr Tyr Asp Ser Phe Lys Leu Gln Thr Lys Glu Phe Gln Val Leu
        35                  40                  45

Lys Ser Leu Gly Lys Leu Ala Met Gly Ser Asp Ser Gln Ser Val Ser
    50                  55                  60

Ser Ser Ser Thr Gln Asp Pro His Arg Gly Arg Gln Thr Leu Gly Ser
65                  70                  75                  80

Leu Arg Gly Leu Ala Lys Ala Lys Pro Glu Ala Ser Phe Gln Val Trp
                85                  90                  95

Asn Lys Asp Ser Ser Ser Lys Asn Leu Ile Pro Arg Leu Gln Lys Ile
            100                 105                 110

Trp Lys Asn Tyr Leu Ser Met Asn Lys Tyr Lys Val Ser Tyr Lys Gly
        115                 120                 125

Pro Gly Pro Gly Ile Lys Phe Ser Ala Glu Ala Leu Arg Cys His Leu
    130                 135                 140

Arg Asp His Val Asn Val Ser Met Val Glu Val Thr Asp Phe Pro Phe
145                 150                 155                 160

Asn Thr Ser Glu Trp Glu Gly Tyr Leu Pro Lys Glu Ser Ile Arg Thr
                165                 170                 175

Lys Ala Gly Pro Trp Gly Arg Cys Ala Val Val Ser Ser Ala Gly Ser
            180                 185                 190

Leu Lys Ser Ser Gln Leu Gly Arg Glu Ile Asp Asp His Asp Ala Val
        195                 200                 205

Leu Arg Phe Asn Gly Ala Pro Thr Ala Asn Phe Gln Gln Asp Val Gly
    210                 215                 220

Thr Lys Thr Thr Ile Arg Leu Met Asn Ser Gln Leu Val Thr Thr Glu
225                 230                 235                 240

Lys Arg Phe Leu Lys Asp Ser Leu Tyr Asn Glu Gly Ile Leu Ile Val
                245                 250                 255

Trp Asp Pro Ser Val Tyr His Ser Asp Ile Pro Lys Trp Tyr Gln Asn
            260                 265                 270

Pro Asp Tyr Asn Phe Phe Asn Asn Tyr Lys Thr Tyr Arg Lys Leu His
        275                 280                 285

Pro Asn Gln Pro Phe Tyr Ile Leu Lys Pro Gln Met Pro Trp Glu Leu
    290                 295                 300

Trp Asp Ile Leu Gln Glu Ile Ser Pro Glu Glu Ile Gln Pro Asn Pro
305                 310                 315                 320

Pro Ser Ser Gly Met Leu Gly Ile Ile Ile Met Met Thr Leu Cys Asp
                325                 330                 335

Gln Val Asp Ile Tyr Glu Phe Leu Pro Ser Lys Arg Lys Thr Asp Val
            340                 345                 350

Cys Tyr Tyr Tyr Gln Lys Phe Phe Asp Ser Ala Cys Thr Met Gly Ala
        355                 360                 365

Tyr His Pro Leu Leu Tyr Glu Lys Asn Leu Val Lys His Leu Asn Gln
    370                 375                 380
```

```
Gly Thr Asp Glu Asp Ile Tyr Leu Leu Gly Lys Ala Thr Leu Pro Gly
385                 390                 395                 400

Phe Arg Thr Ile His Cys
                405

<210> SEQ ID NO 2
<211> LENGTH: 317
<212> TYPE: PRT
<213> ORGANISM: Artificial Sequence
<220> FEATURE:
<223> OTHER INFORMATION: delta89 truncation variant of hST6Gal-I

<400> SEQUENCE: 2

Glu Ala Ser Phe Gln Val Trp Asn Lys Asp Ser Ser Lys Asn Leu
1               5                   10                  15

Ile Pro Arg Leu Gln Lys Ile Trp Lys Asn Tyr Leu Ser Met Asn Lys
                20                  25                  30

Tyr Lys Val Ser Tyr Lys Gly Pro Gly Pro Gly Ile Lys Phe Ser Ala
                35                  40                  45

Glu Ala Leu Arg Cys His Leu Arg Asp His Val Asn Val Ser Met Val
50                  55                  60

Glu Val Thr Asp Phe Pro Phe Asn Thr Ser Glu Trp Glu Gly Tyr Leu
65                  70                  75                  80

Pro Lys Glu Ser Ile Arg Thr Lys Ala Gly Pro Trp Gly Arg Cys Ala
                85                  90                  95

Val Val Ser Ser Ala Gly Ser Leu Lys Ser Ser Gln Leu Gly Arg Glu
                100                 105                 110

Ile Asp Asp His Asp Ala Val Leu Arg Phe Asn Gly Ala Pro Thr Ala
                115                 120                 125

Asn Phe Gln Gln Asp Val Gly Thr Lys Thr Thr Ile Arg Leu Met Asn
130                 135                 140

Ser Gln Leu Val Thr Thr Glu Lys Arg Phe Leu Lys Asp Ser Leu Tyr
145                 150                 155                 160

Asn Glu Gly Ile Leu Ile Val Trp Asp Pro Ser Val Tyr His Ser Asp
                165                 170                 175

Ile Pro Lys Trp Tyr Gln Asn Pro Asp Tyr Asn Phe Phe Asn Asn Tyr
                180                 185                 190

Lys Thr Tyr Arg Lys Leu His Pro Asn Gln Pro Phe Tyr Ile Leu Lys
                195                 200                 205

Pro Gln Met Pro Trp Glu Leu Trp Asp Ile Leu Gln Glu Ile Ser Pro
210                 215                 220

Glu Glu Ile Gln Pro Asn Pro Pro Ser Ser Gly Met Leu Gly Ile Ile
225                 230                 235                 240

Ile Met Met Thr Leu Cys Asp Gln Val Asp Ile Tyr Glu Phe Leu Pro
                245                 250                 255

Ser Lys Arg Lys Thr Asp Val Cys Tyr Tyr Tyr Gln Lys Phe Phe Asp
                260                 265                 270

Ser Ala Cys Thr Met Gly Ala Tyr His Pro Leu Leu Tyr Glu Lys Asn
                275                 280                 285

Leu Val Lys His Leu Asn Gln Gly Thr Asp Glu Asp Ile Tyr Leu Leu
                290                 295                 300

Gly Lys Ala Thr Leu Pro Gly Phe Arg Thr Ile His Cys
305                 310                 315

<210> SEQ ID NO 3
```

<211> LENGTH: 298
<212> TYPE: PRT
<213> ORGANISM: Artificial Sequence
<220> FEATURE:
<223> OTHER INFORMATION: delta108 truncation variant of hST6Gal-I

<400> SEQUENCE: 3

```
Leu Gln Lys Ile Trp Lys Asn Tyr Leu Ser Met Asn Lys Tyr Lys Val
  1               5                  10                  15

Ser Tyr Lys Gly Pro Gly Pro Gly Ile Lys Phe Ser Ala Glu Ala Leu
             20                  25                  30

Arg Cys His Leu Arg Asp His Val Asn Val Ser Met Val Glu Val Thr
         35                  40                  45

Asp Phe Pro Phe Asn Thr Ser Glu Trp Glu Gly Tyr Leu Pro Lys Glu
     50                  55                  60

Ser Ile Arg Thr Lys Ala Gly Pro Trp Gly Arg Cys Ala Val Val Ser
 65                  70                  75                  80

Ser Ala Gly Ser Leu Lys Ser Ser Gln Leu Gly Arg Glu Ile Asp Asp
                 85                  90                  95

His Asp Ala Val Leu Arg Phe Asn Gly Ala Pro Thr Ala Asn Phe Gln
            100                 105                 110

Gln Asp Val Gly Thr Lys Thr Thr Ile Arg Leu Met Asn Ser Gln Leu
        115                 120                 125

Val Thr Thr Glu Lys Arg Phe Leu Lys Asp Ser Leu Tyr Asn Glu Gly
    130                 135                 140

Ile Leu Ile Val Trp Asp Pro Ser Val Tyr His Ser Asp Ile Pro Lys
145                 150                 155                 160

Trp Tyr Gln Asn Pro Asp Tyr Asn Phe Phe Asn Asn Tyr Lys Thr Tyr
                165                 170                 175

Arg Lys Leu His Pro Asn Gln Pro Phe Tyr Ile Leu Lys Pro Gln Met
            180                 185                 190

Pro Trp Glu Leu Trp Asp Ile Leu Gln Glu Ile Ser Pro Glu Glu Ile
        195                 200                 205

Gln Pro Asn Pro Pro Ser Ser Gly Met Leu Gly Ile Ile Met Met Met
    210                 215                 220

Thr Leu Cys Asp Gln Val Asp Ile Tyr Glu Phe Leu Pro Ser Lys Arg
225                 230                 235                 240

Lys Thr Asp Val Cys Tyr Tyr Tyr Gln Lys Phe Phe Asp Ser Ala Cys
                245                 250                 255

Thr Met Gly Ala Tyr His Pro Leu Leu Tyr Glu Lys Asn Leu Val Lys
            260                 265                 270

His Leu Asn Gln Gly Thr Asp Glu Asp Ile Tyr Leu Leu Gly Lys Ala
        275                 280                 285

Thr Leu Pro Gly Phe Arg Thr Ile His Cys
        290                 295
```

<210> SEQ ID NO 4
<211> LENGTH: 1054
<212> TYPE: DNA
<213> ORGANISM: Artificial Sequence
<220> FEATURE:
<223> OTHER INFORMATION: Expression construct Epo-AP-delta89 ST6
      (encoded amino acids of positions 90-406 of hST6Gal-I wild-type
      protein if SEQ ID NO:1, N-terminal methionine added)
<220> FEATURE:
<221> NAME/KEY: CDS
<222> LOCATION: (8)..(1048)
<223> OTHER INFORMATION: open reading frame

```
<400> SEQUENCE: 4 gtcgacc atg ggc gtg cac gaa tgt cct gcc tgg ctg tgg ctg ctg ctg        49
        Met Gly Val His Glu Cys Pro Ala Trp Leu Trp Leu Leu Leu
        1               5                  10 agc ctg ctg tct ctg cct ctg gga ctg cct gtg ctg ggc gcc cct gaa        97
Ser Leu Leu Ser Leu Pro Leu Gly Leu Pro Val Leu Gly Ala Pro Glu
15                  20                  25                  30 gcc tct ttc cag gtg tgg aac aag gac agc agc tcc aag aac ctg atc       145
Ala Ser Phe Gln Val Trp Asn Lys Asp Ser Ser Ser Lys Asn Leu Ile
                35                  40                  45 ccc cgg ctg cag aag atc tgg aag aac tac ctg agc atg aac aag tac       193
Pro Arg Leu Gln Lys Ile Trp Lys Asn Tyr Leu Ser Met Asn Lys Tyr
            50                  55                  60 aag gtg tcc tac aag ggc cct ggc cct ggc atc aag ttt agc gcc gag       241
Lys Val Ser Tyr Lys Gly Pro Gly Pro Gly Ile Lys Phe Ser Ala Glu
        65                  70                  75 gcc ctg aga tgc cac ctg agg gat cac gtg aac gtg tcc atg gtg gaa       289
Ala Leu Arg Cys His Leu Arg Asp His Val Asn Val Ser Met Val Glu
    80                  85                  90 gtg acc gac ttc cca ttc aac acc agc gag tgg gag ggc tac ctg ccc       337
Val Thr Asp Phe Pro Phe Asn Thr Ser Glu Trp Glu Gly Tyr Leu Pro
95                  100                 105                 110 aaa gag agc atc cgg acc aaa gcc ggc cct tgg gga aga tgt gcc gtg       385
Lys Glu Ser Ile Arg Thr Lys Ala Gly Pro Trp Gly Arg Cys Ala Val
                115                 120                 125 gtg tct agc gcc ggc agc ctg aag agt agc cag ctg ggc aga gag atc       433
Val Ser Ser Ala Gly Ser Leu Lys Ser Ser Gln Leu Gly Arg Glu Ile
            130                 135                 140 gac gac cac gac gcc gtg ctg cgg ttc aat ggc gct ccc acc gcc aac       481
Asp Asp His Asp Ala Val Leu Arg Phe Asn Gly Ala Pro Thr Ala Asn
        145                 150                 155 ttc cag cag gac gtg ggc acc aag acc acc atc cgg ctg atg aac tcc       529
Phe Gln Gln Asp Val Gly Thr Lys Thr Thr Ile Arg Leu Met Asn Ser
    160                 165                 170 cag ctc gtg aca acc gag aag cgg ttc ctg aag gac agc ctg tac aac       577
Gln Leu Val Thr Thr Glu Lys Arg Phe Leu Lys Asp Ser Leu Tyr Asn
175                 180                 185                 190 gag ggc atc ctg atc gtg tgg gac ccc agc gtg tac cac agc gac atc       625
Glu Gly Ile Leu Ile Val Trp Asp Pro Ser Val Tyr His Ser Asp Ile
                195                 200                 205 ccc aag tgg tat cag aac ccc gac tac aac ttc ttc aac aac tac aag       673
Pro Lys Trp Tyr Gln Asn Pro Asp Tyr Asn Phe Phe Asn Asn Tyr Lys
            210                 215                 220 acc tac cgg aag ctg cac ccc aac cag ccc ttc tac atc ctg aag ccc       721
Thr Tyr Arg Lys Leu His Pro Asn Gln Pro Phe Tyr Ile Leu Lys Pro
        225                 230                 235 cag atg ccc tgg gag ctg tgg gac att ctg cag gaa atc agc ccc gaa       769
Gln Met Pro Trp Glu Leu Trp Asp Ile Leu Gln Glu Ile Ser Pro Glu
    240                 245                 250 gag atc cag ccc aac ccc cct agc tct ggc atg ctg ggc atc att atc       817
Glu Ile Gln Pro Asn Pro Pro Ser Ser Gly Met Leu Gly Ile Ile Ile
255                 260                 265                 270 atg atg acc ctg tgc gac cag gtg gac atc tac gag ttt ctg ccc tcc       865
Met Met Thr Leu Cys Asp Gln Val Asp Ile Tyr Glu Phe Leu Pro Ser
                275                 280                 285 aag aga aag acc gac gtg tgc tac tac tac cag aag ttc ttc gac agc       913
Lys Arg Lys Thr Asp Val Cys Tyr Tyr Tyr Gln Lys Phe Phe Asp Ser
            290                 295                 300 gcc tgc acc atg gga gcc tac cac cct ctg ctg tac gag aag aac ctc       961
```

```
Ala Cys Thr Met Gly Ala Tyr His Pro Leu Leu Tyr Glu Lys Asn Leu
            305                 310                 315 gtg aag cac ctg aac cag ggc acc gac gag gat atc tac ctg ctg ggc      1009
Val Lys His Leu Asn Gln Gly Thr Asp Glu Asp Ile Tyr Leu Leu Gly
            320                 325                 330 aag gcc acc ctg ccc ggc ttc aga acc atc cac tgc tga ggatcc           1054
Lys Ala Thr Leu Pro Gly Phe Arg Thr Ile His Cys
335                 340                 345
```

<210> SEQ ID NO 5
<211> LENGTH: 346
<212> TYPE: PRT
<213> ORGANISM: Artificial Sequence
<220> FEATURE:
<223> OTHER INFORMATION: Synthetic Construct

<400> SEQUENCE: 5

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Glu Ala Ser
                20                  25                  30

Phe Gln Val Trp Asn Lys Asp Ser Ser Lys Asn Leu Ile Pro Arg
            35                  40                  45

Leu Gln Lys Ile Trp Lys Asn Tyr Leu Ser Met Asn Lys Tyr Lys Val
    50                  55                  60

Ser Tyr Lys Gly Pro Gly Pro Gly Ile Lys Phe Ser Ala Glu Ala Leu
65                  70                  75                  80

Arg Cys His Leu Arg Asp His Val Asn Val Ser Met Val Glu Val Thr
                85                  90                  95

Asp Phe Pro Phe Asn Thr Ser Glu Trp Glu Gly Tyr Leu Pro Lys Glu
            100                 105                 110

Ser Ile Arg Thr Lys Ala Gly Pro Trp Gly Arg Cys Ala Val Val Ser
        115                 120                 125

Ser Ala Gly Ser Leu Lys Ser Ser Gln Leu Gly Arg Glu Ile Asp Asp
    130                 135                 140

His Asp Ala Val Leu Arg Phe Asn Gly Ala Pro Thr Ala Asn Phe Gln
145                 150                 155                 160

Gln Asp Val Gly Thr Lys Thr Thr Ile Arg Leu Met Asn Ser Gln Leu
                165                 170                 175

Val Thr Thr Glu Lys Arg Phe Leu Lys Asp Ser Leu Tyr Asn Glu Gly
            180                 185                 190

Ile Leu Ile Val Trp Asp Pro Ser Val Tyr His Ser Asp Ile Pro Lys
        195                 200                 205

Trp Tyr Gln Asn Pro Asp Tyr Asn Phe Phe Asn Asn Tyr Lys Thr Tyr
    210                 215                 220

Arg Lys Leu His Pro Asn Gln Pro Phe Tyr Ile Leu Lys Pro Gln Met
225                 230                 235                 240

Pro Trp Glu Leu Trp Asp Ile Leu Gln Glu Ile Ser Pro Glu Glu Ile
                245                 250                 255

Gln Pro Asn Pro Pro Ser Ser Gly Met Leu Gly Ile Ile Met Met
            260                 265                 270

Thr Leu Cys Asp Gln Val Asp Ile Tyr Glu Phe Leu Pro Ser Lys Arg
        275                 280                 285

Lys Thr Asp Val Cys Tyr Tyr Tyr Gln Lys Phe Phe Asp Ser Ala Cys
    290                 295                 300

Thr Met Gly Ala Tyr His Pro Leu Leu Tyr Glu Lys Asn Leu Val Lys
```

```
                        305                 310                 315                 320
His Leu Asn Gln Gly Thr Asp Glu Asp Ile Tyr Leu Leu Gly Lys Ala
                325                 330                 335

Thr Leu Pro Gly Phe Arg Thr Ile His Cys
        340                 345

<210> SEQ ID NO 6
<211> LENGTH: 1003
<212> TYPE: DNA
<213> ORGANISM: Artificial Sequence
<220> FEATURE:
<223> OTHER INFORMATION: Expression construct Epo-AP-delta108 ST6
      (encoded amino acids of positions 109-406 of hST6Gal-I wild-
      type protein if SEQ ID NO:1, N-terminal methionine added)
<220> FEATURE:
<221> NAME/KEY: CDS
<222> LOCATION: (8)..(997)
<223> OTHER INFORMATION: open reading frame

<400> SEQUENCE: 6 gtcgacc atg ggc gtg cac gaa tgt cct gcc tgg ctg tgg ctg ctg ctg      49
        Met Gly Val His Glu Cys Pro Ala Trp Leu Trp Leu Leu Leu
            1               5                  10 agc ctg ctg tct ctg cct ctg gga ctg cct gtg ctg ggc gcc cct cct      97
Ser Leu Leu Ser Leu Pro Leu Gly Leu Pro Val Leu Gly Ala Pro Pro
 15                  20                  25                  30 aga ctg cag aag atc tgg aag aac tac ctg agc atg aac aag tac aag     145
Arg Leu Gln Lys Ile Trp Lys Asn Tyr Leu Ser Met Asn Lys Tyr Lys
                 35                  40                  45 gtg tcc tac aag ggc cct ggc cct ggc atc aag ttt agc gcc gag gcc     193
Val Ser Tyr Lys Gly Pro Gly Pro Gly Ile Lys Phe Ser Ala Glu Ala
             50                  55                  60 ctg aga tgc cac ctg agg gat cac gtg aac gtg tcc atg gtg gaa gtg     241
Leu Arg Cys His Leu Arg Asp His Val Asn Val Ser Met Val Glu Val
         65                  70                  75 acc gac ttc cca ttc aac acc agc gag tgg gag ggc tac ctg ccc aaa     289
Thr Asp Phe Pro Phe Asn Thr Ser Glu Trp Glu Gly Tyr Leu Pro Lys
     80                  85                  90 gag agc atc cgg acc aaa gcc ggc cct tgg gga aga tgt gcc gtg gtg     337
Glu Ser Ile Arg Thr Lys Ala Gly Pro Trp Gly Arg Cys Ala Val Val
 95                 100                 105                 110 tct agc gcc ggc agc ctg aag agt agc cag ctg ggc aga gag atc gac     385
Ser Ser Ala Gly Ser Leu Lys Ser Ser Gln Leu Gly Arg Glu Ile Asp
                115                 120                 125 gac cac gac gcc gtg ctg cgg ttc aat ggc gct ccc acc gcc aac ttc     433
Asp His Asp Ala Val Leu Arg Phe Asn Gly Ala Pro Thr Ala Asn Phe
            130                 135                 140 cag cag gac gtg ggc acc aag acc acc atc cgg ctg atg aac tcc cag     481
Gln Gln Asp Val Gly Thr Lys Thr Thr Ile Arg Leu Met Asn Ser Gln
        145                 150                 155 ctc gtg aca acc gag aag cgg ttc ctg aag gac agc ctg tac aac gag     529
Leu Val Thr Thr Glu Lys Arg Phe Leu Lys Asp Ser Leu Tyr Asn Glu
    160                 165                 170 ggc atc ctg atc gtg tgg gac ccc agc gtg tac cac agc gac atc ccc     577
Gly Ile Leu Ile Val Trp Asp Pro Ser Val Tyr His Ser Asp Ile Pro
175                 180                 185                 190 aag tgg tat cag aac ccc gac tac aac ttc ttc aac aac tac aag acc     625
Lys Trp Tyr Gln Asn Pro Asp Tyr Asn Phe Phe Asn Asn Tyr Lys Thr
                195                 200                 205 tac cgg aag ctg cac ccc aac cag ccc ttc tac atc ctg aag ccc cag     673
Tyr Arg Lys Leu His Pro Asn Gln Pro Phe Tyr Ile Leu Lys Pro Gln
            210                 215                 220
```

```
atg ccc tgg gag ctg tgg gac att ctg cag gaa atc agc ccc gaa gag       721
Met Pro Trp Glu Leu Trp Asp Ile Leu Gln Glu Ile Ser Pro Glu Glu
        225                 230                 235 atc cag ccc aac ccc cct agc tct ggc atg ctg ggc atc att atc atg       769
Ile Gln Pro Asn Pro Pro Ser Ser Gly Met Leu Gly Ile Ile Ile Met
    240                 245                 250 atg acc ctg tgc gac cag gtg gac atc tac gag ttt ctg ccc tcc aag       817
Met Thr Leu Cys Asp Gln Val Asp Ile Tyr Glu Phe Leu Pro Ser Lys
255                 260                 265                 270 aga aag acc gac gtg tgc tac tac cag aag ttc ttc gac agc gcc           865
Arg Lys Thr Asp Val Cys Tyr Tyr Gln Lys Phe Phe Asp Ser Ala
                275                 280                 285 tgc acc atg gga gcc tac cac cct ctg ctg tac gag aag aac ctc gtg       913
Cys Thr Met Gly Ala Tyr His Pro Leu Leu Tyr Glu Lys Asn Leu Val
            290                 295                 300 aag cac ctg aac cag ggc acc gac gag gat atc tac ctg ctg ggc aag       961
Lys His Leu Asn Gln Gly Thr Asp Glu Asp Ile Tyr Leu Leu Gly Lys
        305                 310                 315 gcc acc ctg ccc ggc ttc aga acc atc cac tgc tga ggatcc                1003
Ala Thr Leu Pro Gly Phe Arg Thr Ile His Cys
    320                 325

<210> SEQ ID NO 7
<211> LENGTH: 329
<212> TYPE: PRT
<213> ORGANISM: Artificial Sequence
<220> FEATURE:
<223> OTHER INFORMATION: Synthetic Construct

<400> SEQUENCE: 7

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Gln Lys Ile Trp Lys Asn Tyr Leu Ser Met Asn Lys Tyr Lys Val Ser
        35                  40                  45

Tyr Lys Gly Pro Gly Pro Gly Ile Lys Phe Ser Ala Glu Ala Leu Arg
    50                  55                  60

Cys His Leu Arg Asp His Val Asn Val Ser Met Val Glu Val Thr Asp
65                  70                  75                  80

Phe Pro Phe Asn Thr Ser Glu Trp Glu Gly Tyr Leu Pro Lys Glu Ser
                85                  90                  95

Ile Arg Thr Lys Ala Gly Pro Trp Gly Arg Cys Ala Val Val Ser Ser
            100                 105                 110

Ala Gly Ser Leu Lys Ser Ser Gln Leu Gly Arg Glu Ile Asp Asp His
        115                 120                 125

Asp Ala Val Leu Arg Phe Asn Gly Ala Pro Thr Ala Asn Phe Gln Gln
    130                 135                 140

Asp Val Gly Thr Lys Thr Thr Ile Arg Leu Met Asn Ser Gln Leu Val
145                 150                 155                 160

Thr Thr Glu Lys Arg Phe Leu Lys Asp Ser Leu Tyr Asn Glu Gly Ile
                165                 170                 175

Leu Ile Val Trp Asp Pro Ser Val Tyr His Ser Asp Ile Pro Lys Trp
            180                 185                 190

Tyr Gln Asn Pro Asp Tyr Asn Phe Phe Asn Asn Tyr Lys Thr Tyr Arg
        195                 200                 205

Lys Leu His Pro Asn Gln Pro Phe Tyr Ile Leu Lys Pro Gln Met Pro
```

-continued

```
                210                 215                 220
Trp Glu Leu Trp Asp Ile Leu Gln Glu Ile Ser Pro Glu Glu Ile Gln
225                 230                 235                 240

Pro Asn Pro Pro Ser Ser Gly Met Leu Gly Ile Ile Ile Met Met Thr
                245                 250                 255

Leu Cys Asp Gln Val Asp Ile Tyr Glu Phe Leu Pro Ser Lys Arg Lys
                260                 265                 270

Thr Asp Val Cys Tyr Tyr Gln Lys Phe Phe Asp Ser Ala Cys Thr
                275                 280                 285

Met Gly Ala Tyr His Pro Leu Leu Tyr Glu Lys Asn Leu Val Lys His
                290                 295                 300

Leu Asn Gln Gly Thr Asp Glu Asp Ile Tyr Leu Leu Gly Lys Ala Thr
305                 310                 315                 320

Leu Pro Gly Phe Arg Thr Ile His Cys
                325
```

QUANTITATIVE CONTROL OF SIALYLATION AND SPECIFIC MONO-SIALYLATION

CROSS-REFERENCE TO RELATED APPLICATIONS

This application is a continuation of International Patent Application No. PCT/EP2014/064213 filed Jul. 3, 2014, which claims priority to European Patent Application No. 13175347.7 filed Jul. 5, 2013, the disclosures of which are hereby incorporated by reference in their entirety.

FIELD

The present disclosure is directed to the use of certain glycosyltransferase variants having N-terminal truncation deletions. It was found that the combination of two different truncation variants of human β-galactoside-α-2,6-sialyltransferase I (hST6Gal-I) exhibited different specific sialyltransferase enzymatic activities. In one example, under conditions wherein the first variant Δ89 hST6Gal-I catalyzed formation of bi-sialylated target molecules the second variant Δ108 hST6Gal-I catalyzed formation of mono-sialylated target molecules. Thus, disclosed are variants of mammalian glycosyltransferase, nucleic acids encoding the same, methods and means for recombinantly producing the variants of mammalian glycosyltransferase and use thereof, particularly for sialylating in a quantitatively controlled manner terminal acceptor groups of glycan moieties being part of glycoproteins such as immunoglobulins.

BACKGROUND

Transferases (EC 2) catalyze transfer of a functional group from one substance to another. Glycosyltransferases, a superfamily of enzymes, are involved in synthesizing the carbohydrate portions of glycoproteins, glycolipids and glycosaminoglycans. Specific glycosyltransferases synthesize oligosaccharides by the sequential transfer of the monosaccharide moiety of an activated sugar donor to an acceptor molecule. Hence, a "glycosyltransferase" catalyzes the transfer of a sugar moiety from its nucleotide donor to an acceptor moiety of a polypeptide, lipid, glycoprotein or glycolipid. This process is also known as "glycosylation". A carbohydrate portion which is structural part of e.g. a glycoprotein is also referred to as "glycan". Glycans constitute the most prevalent of all known post-translational protein modifications. Glycans are involved in a wide array of biological recognition processes as diverse as adhesion, immune response, neural cell migration and axonal extension. As structural part of glycoproteins glycans also have a role in protein folding and the support of protein stability and biological activity.

In glycosyltransferase catalysis, the monosaccharide units glucose (Glc), galactose (Gal), N-acetylglucosamine (GlcNAc), N-acetylgalactosamine (GalNAc), glucuronic acid (GlcUA), galacturonic acid (GalUA) and xylose are activated as uridine diphosphate (UDP)-α-D derivatives; arabinose is activated as a UDP-β-L derivative; mannose (Man) and fucose are activated as GDP-α-D and GDP-β-L derivatives, respectively; and sialic acid (=Neu5Ac; =SA) is activated as a CMP derivative of β-D-Neu5Ac.

Many different glycosyltransferases contribute to the synthesis of glycans. The structural diversity of carbohydrate portions of glycoproteins is particularly large and is determined by complex biosynthetic pathways. In eukaryotes the biosynthesis of the glycan-part of glycoproteins takes place in the lumen of the endoplasmatic reticulum ("ER") and the Golgi apparatus. A single (branched or linear) carbohydrate chain of a glycoprotein is typically a N- or an O-linked glycan. During post-translational processing, carbohydrates are typically connected to the polypeptide via asparagine ("N-linked glycosylation"), or via serine or threonine ("O-linked glycosylation"). Synthesis of a glycan, no matter whether N- or O-linked (="N—/O-linked") is effected by the activity of several different membrane-anchored glycosyltransferases. A glycoprotein may comprise one or more glycan-connected amino acids (="glycosylation sites"). A specific glycan structure may be linear or branched. Branching is a notable feature of carbohydrates which is in contrast to the linear nature typical for DNA, RNA, and polypeptides. Combined with the large heterogeneity of their basic building blocks, the monosaccharides, glycan structures exhibit high diversity. Furthermore, in members of a particular glycoprotein species the structure of a glycan attached to a particular glycosylation site may vary, thus resulting in microheterogeneity of the respective glycoprotein species, i.e. in a species sharing the same amino acid sequence of the poypeptide portion.

A sialyltransferase (="ST") is a glycosyltransferase that catalyzes transfer of a sialic acid (=5-N-acetylneuramic acid=Neu5Ac=NANA) residue from a donor compound to (i) a terminal monosaccharide acceptor group of a glycolipid or a ganglioside, or (ii) to a terminal monosaccharide acceptor group of an N—/O-linked glycan of a glycoprotein. For mammalian sialyltransferases including human ST species there is a common donor compound which is cytidine-5'-monophospho-N-acetylneuraminic acid (=CMP-Neu5Ac=CMP-NANA). Transfer of a sialic acid residue is also referred to as "sialylating" and "sialylation".

In the glycan structure of a sialylated glycoprotein the (one or more) sialyl moiety (moieties) is (are) usually found in terminal position of the oligosaccharide. Owing to the terminal, i.e. exposed position, sialic acid can participate in many different biological recognition phenomena and serve in different kinds of biological interactions. In a glycoprotein more than one sialylation site may be present, i.e. a site capable of serving as a substrate for a sialyltransferase and being an acceptor group suitable for the transfer of a sialic acid residue. Such more than one site can in principle be the termini of a plurality of linear glycan portions anchored at different glycosylation sites of the glycoprotein. Additionally, a branched glycan may have a plurality of sites where sialylation can occur.

According to current knowledge, a terminal sialic acid residue can be found (i) α2→3 (α2,3) linked to galactosyl-R, (ii) α2→6 (α2,6) linked to galactosyl-R, (iii) α2→6 (α2,6) linked to N-acetylgalactosaminidyl-R, (iv) α2→6 (α2,6) linked to N-acetylglucosaminidyl-R, and (v) α2→8/9 (α2,8/9) linked to sialidyl-R, wherein —R denotes the rest of the acceptor substrate moiety. Hence, a sialyltransferase active in the biosynthesis of sialylconjugates (="sialylation") is generally named and classified according to its respective monosaccharide acceptor substrate and according to the 3, 6 or 8/9 position of the glycosidic bond it catalyzes. Accordingly, in the literature known to the art, e.g. in Patel R Y, et al, Glycobiology 16 (2006) 108-116, reference to eukaryotic sialyltransferases is made such as (i) ST3Gal, (ii) ST6Gal, (iii) ST6GalNAc, or (v) ST8Sia, depending on the hydroxyl position of the acceptor sugar residue to which the Neu5Ac residue is transferred while forming a glycosidic bond. Reference to sialyltransferases in a more generic way can also be made e.g. as ST3, ST6, ST8; thus, "ST6" specifically encompasses the sialyltransferases catalyzing an α2,6 sialylation.

The disaccharide moiety β-D-galactosyl-1,4-N-acetyl-β-D-glucosamine (=Galβ1,4GlcNAc) is a frequent terminal residue of the antennae of N-linked glycans of glycoproteins, but may be also present in O-linked glycans and in glycolipids. The enzyme β-galactoside-α2,6-sialyltransferase (="ST6Gal") is able to catalyze α2,6-sialylation of a terminal Galβ1,4GlcNAc of a glycan or a branch of a glycan (="antenna"). For general aspects thereof, reference is made to the document of DallOlio F. Glycoconjugate Journal 17 (2000) 669-676. In human and in other mammals there appear to be several species of ST6Gal. The present disclosure particularly deals with human β-galactoside-α-2,6-sialyltransferase I (=hST6Gal-I; EC 2.4.99.1 according to IUBMB Enzyme Nomenclature), but is not limited thereto.

The ST6 group of sialyltransferases comprises 2 subgroups, ST6Gal and ST6GalNAc. The activity of ST6Gal enzymes catalyzes transfer of a Neu5Ac residue to the C6 hydroxyl group of a free galactosyl residue being part of terminal Galβ1,4GlcNAc in a glycan or an antenna of a glycan, thereby forming in the glycan a terminal sialic acid residue α2→6 linked to the galactosyl residue of the Galβ1, 4GlcNAc moiety. The resulting newly formed terminal moiety in the glycan is Neu5Acα2,6Galβ1,4GlcNAc.

The wild-type polypeptide of human β-galactoside-α-2, 6-sialyltransferase I (hST6Gal-I) at the time of filing of the present document was disclosed as "UniProtKB/Swiss-Prot: P15907.1" in the publically accessible NCBI database (http://www.ncbi.nlm.nih.gov/protein/115445). Further information including coding sequences are provided as hyperlinks compiled within the database entry "Gene ID: 6480" (http://www.ncbi.nlm.nih.gov/gene/6480).

Mammalian sialyltransferases share with other mammalian Golgi-resident glycosyltransferases a so-called "type II architecture" with (i) a short cytoplasmic N-terminal tail, (ii) a transmembrane fragment followed by (iii) a stem region of variable length and (iv) a C-terminal catalytic domain facing the lumen of the Golgi apparatus (Donadio S. et al. in Biochimie 85 (2003) 311-321). Mammalian sialyltransferases appear to display significant sequence homology in their catalytic domain.

Donadio S. et al. expressed several N-terminally truncated variants of hST6Gal-I in CHO cells and found that N-terminal deletions comprising the first 35, 48, 60 and 89 amino acids yielded mutant enzymes which nevertheless were still active in transferring sialic acid to exogenous acceptors.

Glycosylation is an important posttranslational modification of proteins influencing protein folding, stability and regulation of the biological activity. The sialyl mojety (=sialic acid, 5-N-acetylneuramic acid, Neu5Ac) is usually exposed at the terminal position of N-glycosylation and therefore, a major contributor to biological recognition and ligand function, e.g. IgG featuring terminal sialic acids were shown to induce less inflammatory response and increased serum half-life.

The use of glycosyltransferases for enzymatic synthesis of defined glycan structures is becoming a tool to direct N-glycosylation of therapeutic proteins such as antibodies. Since glycosyltransferases of prokaryotic origin usually do not act on complex glycoprotein structures, sialyltransferases of mammalian origin are preferred. For example, Barb et al. (2009) prepared highly potent sialylated forms of the Fc fragment of immunoglobulin G using isolated human ST6Gal-I. However, the access to recombinant ST6Gal-I for therapeutic applications is still limited due to low expression and/or poor activity in various hosts (*Pichia pastoris, Spodoptera frugiperda* and *E. coli*).

It is known to the art that mammalian glycosyltransferases can be used advantageously for in vitro sialylating antennal acceptor sites of a complex target molecule such as a glycoprotein or a glycolipid. However, there still is a lack of means and methods to perform sialylation in a quantitatively controlled fashion, particularly with regards to target molecules with two or more acceptor sites capable of being sialylated. That is to say, it is desirable to provide means, methods and conditions allowing to sialylate just one out of several acceptor sites, as opposed to sialylating two or more, or even all acceptor sites of the target molecule. It is further desirable to control in a batch sialylation reaction mixture the balance between single-event sialylation of the target molecule and multiple event sialylation thereof.

Surprisingly, it was found initially that the two truncated variants Δ89 hST6Gal-I and Δ108 hST6Gal-I displayed different sialylation activities in-vitro on antibodies, but also on other target molecules. Apparently, the IgG-Fc antennal glycan G2 has two galactose moieties at the termini of the branches which can be sialylated. Under identical reaction conditions, Δ89 hST6Gal-I preferably catalyzes the synthesis of bi-sialylated glycans (G2+2SA), whereas the variant Δ108 hST6Gal-I synthesizes mono-sialylated glycans (G2+ 1SA). Therefore, both enzymes are suitable tools for the selective sialylation of glycan structures, particularly of N-glycans.

The original finding by the present inventors is that the Δ108 hST6Gal-I variant of human β-galactoside-α-2,6-sialyltransferase I is mainly capable of adding only a single sialyl residue to a target molecule with two or more antennal acceptor sites. In contrast, the enzymatic activity of human β-galactoside-α-2,6-sialyltransferase I and specific variants thereof such as Δ89 hST6Gal-I leads to multiple sialylation of the target molecule. Thus, by way of using Δ108 hST6Gal-I alone, for example in a batch process, a mono-sialylated target molecule can be produced from a target molecule with two or more non-sialylated antennal acceptor sites.

This paves the way for a number of different approaches, particularly in the field of in vitro glycoengineering of immunoglobulins, and also of other glycosylated target molecules. Here specifically and exemplarily a method is provided resulting in the production of mono-sialylated and bi-sialylated immunoglobulin G molecules, wherein the ration thereof is controlled by way of controlling the amounts of (i) Δ108 hST6Gal-I enzymatic activity and (ii) enzymatic activity of a human β-galactoside-α-2,6-sialyltransferase I capable of sialylating the acceptor sites of the target molecule in a saturating way. However, a number of other in vitro sialylation approaches with quantitative sialylation control of the target molecule to be sialylated become feasible and can be deduced from the present disclosure.

In a specific embodiment this document discloses the high-yield expression of two different variants of human β-galactoside-α-2,6-sialyltransferase I (hST6Gal-I, EC 2.4.99.1; data base entry P15907) by transient gene expression in HEK293 cells with yields up to 100 mg/L. The two variants were found to feature surprisingly distinct sialylation activities.

SUMMARY OF THE DISCLOSURE

In a first aspect there is disclosed the use of N-terminally truncated human β-galactoside-α-2,6-sialyltransferase I of SEQ ID NO:3 (Δ108 hST6Gal-I) for specifically forming a mono-sialylated target molecule from a target molecule, wherein the target molecule is selected from a glycoprotein or a glycolipid, wherein the target molecule comprises a plurality of antennal target moieties having as terminal structure a β-D-galactosyl-1,4-N-acetyl-β-D-glucosamine moiety with a hydroxyl group at the C6 position in the galactosyl residue, wherein the mono-sialylated target molecule comprises a single sialylated terminal antennal target moiety, and wherein the sialylated terminal antennal target moiety comprises one N-acetylneuraminyl-α2,6-β-D-galactosyl-1,4-N-acetyl-β-D-glucosamine residue.

In a further aspect there is disclosed a method for producing in vitro a sialylated target molecule with a single sialyl residue added to one antennal terminal structure of the target molecule, the method comprising the steps of (a) providing a composition comprising (i) the target molecule, the target molecule being selected from a glycoprotein and a glycolipid, the target molecule comprising a plurality of antennae, at least two of the antennae each having as terminal structure a β-D-galactosyl-1,4-N-acetyl-β-D-glucosamine moiety with a hydroxyl group at the C6 position in the galactosyl residue; (ii) N-terminally truncated human β-galactoside-α-2,6-sialyltransferase I of SEQ ID NO:3 (Δ108 hST6Gal-I); (iii) cytidine-5'-monophospho-N-acetylneuraminic acid, or a functional equivalent thereof, as donor compound for a sialyltransferase-catalyzed reaction; (b) incubating the composition of step (a) under conditions permitting glycosyltransferase enzymatic activity, thereby forming per target molecule a single terminal antennal N-acetylneuraminyl-α2,6-β-D-galactosyl-1,4-N-acetyl-β-D-glucosamine residue (=α2,6 sialylated terminal antennal residue); thereby producing in vitro the sialylated target molecule with a single sialyl residue added to one antennal terminal structure of the target molecule.

In a yet a further aspect there is disclosed a mono-sialylated target molecule selected from a glycoprotein and a glycolipid, the mono-sialylated target molecule being obtainable by a method as disclosed herein.

In a yet a further aspect there is disclosed a composition comprising an aqueous buffer permitting glycosyltransferase enzymatic activity, the composition further comprising: (a) a glycosylated target molecule, the target molecule being selected from a glycoprotein and a glycolipid, the target molecule comprising a plurality of antennae, at least two of the antennae each having as terminal structure a β-D-galactosyl-1,4-N-acetyl-β-D-glucosamine moiety with a hydroxyl group at the C6 position in the galactosyl residue; (b) N-terminally truncated human β-galactoside-α-2,6-sialyltransferase I of SEQ ID NO:2 (Δ89 hST6Gal-I) or a soluble N-terminally truncated human β-galactoside-α-2,6-sialyltransferase I variant with a sialyltransferase enzymatic activity higher or equal to that of Δ89 hST6Gal-I; (c) N-terminally truncated human 3-galactoside-α-2,6-sialyltransferase I of SEQ ID NO:3 (Δ108 hST6Gal-I); (d) cytidine-5'-monophospho-N-acetylneuraminic acid, or a functional equivalent thereof, as donor compound for a sialyltransferase-catalyzed reaction.

In a yet a further aspect there is disclosed the use of a composition as disclosed herein for producing in vitro and under conditions permitting glycosyltransferase enzymatic activity a sialylated target molecule having one or more sialyl residue(s) added to one or more antennal terminal structure(s) of the target molecule.

In a yet a further aspect there is disclosed a method for producing in vitro a sialylated target molecule with a controlled quantity of sialyl residues added to one or more antennal terminal structure(s) of the target molecule, the target molecule being selected from a glycoprotein and a glycolipid, the target molecule comprising a plurality of antennae, at least two of the antennae each having as terminal structure a β-D-galactosyl-1,4-N-acetyl-β-D-glucosamine moiety with a hydroxyl group at the C6 position in the galactosyl residue, the method comprising the steps of (a) providing a composition as disclosed herein; (b) incubating the composition of step (a) under conditions permitting glycosyltransferase enzymatic activity and for a predetermined time interval, thereby forming terminal antennal N-acetylneuraminyl-α2,6-β-D-galactosyl-1,4-N-acetyl-β-D-glucosamine residue(s) [=α2,6 sialylated terminal antennal residue(s)], wherein Δ89 hST6Gal-I catalyzes formation of bi-sialylated IgG and Δ108 hST6Gal-I catalyzes formation of mono-sialylated IgG; thereby producing in vitro the sialylated target molecule with a controlled quantity of sialyl residues added to one or more antennal terminal structure(s) of the target molecule.

In a yet a further aspect there is disclosed a preparation of glycosylated target molecules, the target molecules being immunoglobulin molecules of the IgG class, wherein the amounts of mono- and bi-sialylated target molecules in the preparation are controlled quantities, the preparation being obtained by a method as disclosed herein.

DETAILED DESCRIPTION

Figure 1:
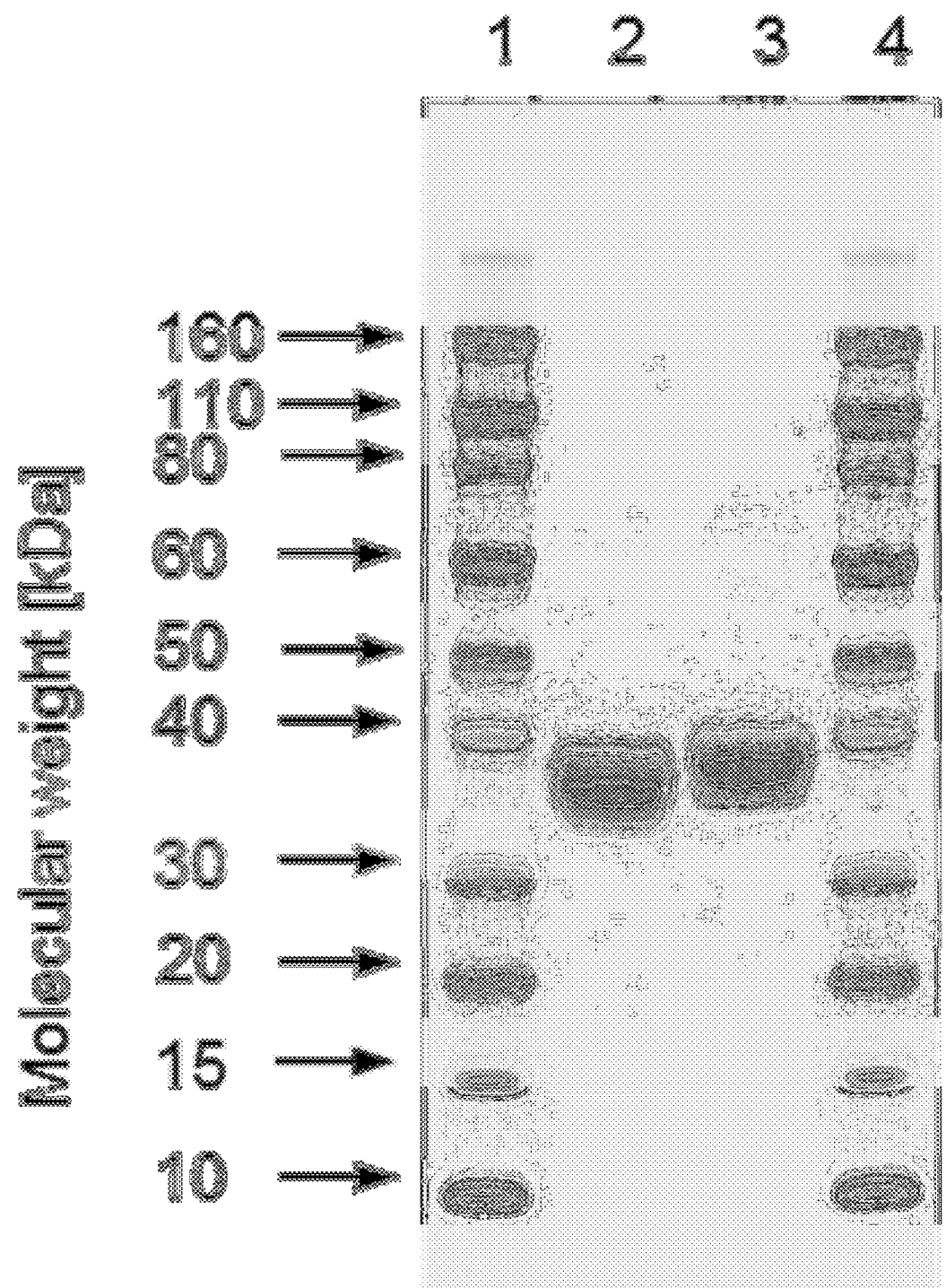
FIG. 1 SDS-PAGE of purified recombinant hST6Gal-I variants expressed in HEK cells. Lanes 1 and 4: molecular weight marker; lane 2: Purified enzyme delta108 hST6Gal-I, 5 µg were loaded onto the gel; Lane 3: Purified enzyme delta89 hST6Gal-I, 5 µg were loaded onto the gel.

The terms "a", "an" and "the" generally include plural referents, unless the context clearly indicates otherwise. As used herein, "plurality" is understood to mean more than one. For example, a plurality refers to at least two, three, four, five, or more. Unless specifically stated or obvious from context, as used herein, the term "or" is understood to be inclusive.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The term "amino acid" generally refers to any monomer unit that can be incorporated into a peptide, polypeptide, or protein. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). In cases where "X" residues are undefined, these should be defined as "any amino acid." The structures of these twenty natural amino acids are shown in, e.g., Stryer et al., Biochemistry, 5th ed., Freeman and Company (2002). Additional amino acids, such as selenocysteine and pyrrolysine, can also be genetically coded for (Stadtman (1996) "Selenocysteine," Annu Rev Biochem. 65:83-100 and Ibba et al. (2002) "Genetic code: introducing pyrrolysine," Curr Biol. 12(13):R464-R466). The term "amino acid" also includes unnatural amino acids, modified amino acids (e.g., having modified side chains and/or backbones), and amino acid analogs. See, e.g., Zhang et al. (2004) "Selective incorporation of 5-hydroxytryptophan into proteins in mammalian cells," Proc. Natl. Acad. Sci. U.S.A. 101(24):8882-8887, Anderson et al. (2004) "An expanded genetic code with a functional quadruplet codon" Proc. Natl. Acad. Sci. U.S.A. 101(20):7566-7571, Ikeda et al. (2003) "Synthesis of a novel histidine analogue and its efficient incorporation into a protein in vivo," Protein Eng. Des. Sel. 16(9):699-706, Chin et al. (2003) "An Expanded Eukaryotic Genetic Code," Science 301(5635):964-967, James et al. (2001) "Kinetic characterization of ribonuclease S mutants containing photoisomerizable phenylazophenylalanine residues," Protein Eng. Des. Sel. 14(12):983-991, Kohrer et al. (2001) "Import of amber and ochre suppressor tRNAs into mammalian cells: A general approach to site-specific insertion of amino acid analogues into proteins," Proc. Natl. Acad. Sci. U.S.A. 98(25): 14310-14315, Bacher et al. (2001) "Selection and Characterization of Escherichia coli Variants Capable of Growth on an Otherwise Toxic Tryptophan Analogue," J. Bacteriol. 183(18):5414-5425, Hamano-Takaku et al. (2000) "A Mutant Escherichia coli Tyrosyl-tRNA Synthetase Utilizes the Unnatural Amino Acid Azatyrosine More Efficiently than Tyrosine," J. Biol. Chem. 275(51):40324-40328, and Budisa et al. (2001) "Proteins with {beta}-(thienopyrrolyl)alanines as alternative chromophores and pharmaceutically active amino acids," Protein Sci. 10(7): 1281-1292. To further illustrate, an amino acid is typically an organic acid that includes a substituted or unsubstituted amino group, a substituted or unsubstituted carboxy group, and one or more side chains or groups, or analogs of any of these groups. Exemplary side chains include, e.g., thiol, seleno, sulfonyl, alkyl, aryl, acyl, keto, azido, hydroxyl, hydrazine, cyano, halo, hydrazide, alkenyl, alkynl, ether, borate, boronate, phospho, phosphono, phosphine, heterocyclic, enone, imine, aldehyde, ester, thioacid, hydroxylamine, or any combination of these groups. Other representative amino acids include, but are not limited to, amino acids comprising photoactivatable cross-linkers, metal binding amino acids, spin-labeled amino acids, fluorescent amino acids, metal-containing amino acids, amino acids with novel functional groups, amino acids that covalently or noncovalently interact with other molecules, photocaged and/or photoisomerizable amino acids, radioactive amino acids, amino acids comprising biotin or a biotin analog, glycosylated amino acids, other carbohydrate modified amino acids, amino acids comprising polyethylene glycol or polyether, heavy atom substituted amino acids, chemically cleavable and/or photocleavable amino acids, carbon-linked sugar-containing amino acids, redox-active amino acids, amino thioacid containing amino acids, and amino acids comprising one or more toxic moieties.

The term "protein" refers to a polypeptide chain (amino acid sequence) as a product of the ribosomal translation process, wherein the polypeptide chain has undergone post-translational folding processes resulting in three-dimensional protein structure. The term "protein" also encompasses polypeptides with one or more posttranslational modifications such as (but not limited to) glycosylation, phosphorylation, acetylation and ubiquitination.

Any protein as disclosed herein, particularly recombinantly produced protein as disclosed herein, may in a specific embodiment comprise a "protein tag" which is a peptide sequence genetically grafted onto the recombinant protein. A protein tag may comprise a linker sequence with a specific protease claeavage site to facilitate removal of the tag by proteolysis. As a specific embodiment, an "affinity tag" is appended to a target protein so that the target can be purified from its crude biological source using an affinity technique. For example, the source can be a transformed host organism expressing the target protein or a culture supernatant into which the target protein was secreted by the transformed host organism. Specific embodiments of an affinity tag include chitin binding protein (CBP), maltose binding protein (MBP), and glutathione-S-transferase (GST). The poly(His) tag is a widely-used protein tag which facilitates binding to certain metal chelating matrices.

The term "chimeric protein", "fusion protein" or "fusion polypeptide" refers to a protein whose amino acid sequence represents a fusion product of subsequences of the amino acid sequences from at least two distinct proteins. A fusion protein typically is not produced by direct manipulation of amino acid sequences, but, rather, is expressed from a "chimeric" gene that encodes the chimeric amino acid sequence.

The term "recombinant" refers to an amino acid sequence or a nucleotide sequence that has been intentionally modified by recombinant methods. By the term "recombinant nucleic acid" herein is meant a nucleic acid, originally formed in vitro, in general, by the manipulation of a nucleic acid by endonucleases, in a form not normally found in nature. Thus an isolated, mutant DNA polymerase nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. A "recombinant protein" or "recombinantly produced protein" is a protein made using recombinant techniques, i.e., through the expression of a recombinant nucleic acid as depicted above.

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation.

The term "host cell" refers to both single-cellular prokaryote and eukaryote organisms (e.g., mammalian cells, insect cells, bacteria, yeast, and actinomycetes) and single cells from higher order plants or animals when being grown in cell culture.

The term "vector" refers to a piece of DNA, typically double-stranded, which may have inserted into it a piece of foreign DNA. The vector or may be, for example, of plasmid origin. Vectors contain "replicon" polynucleotide sequences that facilitate the autonomous replication of the vector in a host cell. Foreign DNA is defined as heterologous DNA, which is DNA not naturally found in the host cell, which, for example, replicates the vector molecule, encodes a selectable or screenable marker, or encodes a transgene. The vector is used to transport the foreign or heterologous DNA into a suitable host cell. Once in the host cell, the vector can replicate independently of or coincidental with the host chromosomal DNA, and several copies of the vector and its inserted DNA can be generated. In addition, the vector can also contain the necessary elements that permit transcription of the inserted DNA into an mRNA molecule or otherwise cause replication of the inserted DNA into multiple copies of RNA. Some expression vectors additionally contain sequence elements adjacent to the inserted DNA that increase the half-life of the expressed mRNA and/or allow translation of the mRNA into a protein molecule. Many molecules of mRNA and polypeptide encoded by the inserted DNA can thus be rapidly synthesized.

The terms "nucleic acid" or "polynucleotide" can be used interchangeably and refer to a polymer that can be corresponded to a ribose nucleic acid (RNA) or deoxyribose nucleic acid (DNA) polymer, or an analog thereof. This includes polymers of nucleotides such as RNA and DNA, as well as synthetic forms, modified (e.g., chemically or biochemically modified) forms thereof, and mixed polymers (e.g., including both RNA and DNA subunits). Exemplary modifications include methylation, substitution of one or more of the naturally occurring nucleotides with an analog, internucleotide modifications such as uncharged linkages (e.g., methyl phosphonates, phosphotriesters, phosphoamidates, carbamates, and the like), pendent moieties (e.g., polypeptides), intercalators (e.g., acridine, psoralen, and the like), chelators, alkylators, and modified linkages (e.g., alpha anomeric nucleic acids and the like). Also included are synthetic molecules that mimic polynucleotides in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids as described in Nielsen et al. (Science 254:1497-1500, 1991). A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, and a primer. A nucleic acid can be, e.g., single-stranded, double-stranded, or triple-stranded and is not limited to any particular length. Unless otherwise indicated, a particular nucleic acid sequence comprises or encodes complementary sequences, in addition to any sequence explicitly indicated.

The term "glycosylation" denotes the chemical reaction of covalently coupling a glycosyl residue to an acceptor group. One specific acceptor group is a hydroxyl group, e.g. a hydroxyl group of another sugar. "Sialylation" is a specific form of glycosylation wherein the acceptor group is reacted with a sialic acid (=N-acetylneuraminic acid) residue. Such a reaction is typically catalyzed by a sialyltransferase enzyme using cytidine-5'-monophospho-N-acetyl-neuraminic acid as donor compound or co-substrate.

"Sialylation" is a specific embodiment of a result of glycosyltransferase enzymatic activity (sialyltransferase enzymatic activity in the particular case), under conditions permitting the same. Generally, the skilled person appreciates that the aqueous buffer in which a glycosyltransferase enzymatic reaction can be performed (="permitting glycosyltransferase enzymatic activity") needs to be buffered using a buffer salt such as Tris, MES, phosphate, acetate, or another buffer salt specifically capable of buffering in the pH range of pH 6 to pH 8, more specifically in the range of pH 6 to pH 7, even more specifically capable of buffering a solution of about pH 6.5. The buffer may further contain a neutral salt such as but not limited to NaCl. Further, in particular embodiments the skilled person may consider adding to the aqueous buffer a salt comprising a divalent ion such as $Mg^{2+}$ or $Mn^{2+}$, e.g. but not limited to $MgCl_2$ and $MnCl_2$. Conditions permitting glycosyltransferase enzymatic activity known to the art include ambient (room) temperature, but more generally temperatures in the range of 0° C. to 40° C., particularly 10° C. to 30° C., particularly 20° C.

The term "glycan" refers to a poly- or oligosaccharide, i.e. to a multimeric compound which upon acid hydrolysis yields a plurality of monosachharides. A glycoprotein comprises one or more glycan moieties which are covalently coupled to side groups of the polypeptide chain, typically via asparagine or arginine ("N-linked glycosylation") or via serine or threonine ("O-linked glycosylation").

The use of glycosyltransferases for enzymatic synthesis of complex glycan structures is an attractive approach to obtain complex bioactive glycoproteins. E.g. Barb et al. Biochemistry 48 (2009) 9705-9707 prepared highly potent sialylated forms of the Fc fragment of immunoglobulin G using isolated human ST6Gal-I. However, growing interest in the therapeutic application of glycoproteins leads to an increasing demand of glycosyltransferases including sialyltransferases. Different strategies to increase or modify the sialylation of glycoproteins were described by Bork K. et al. J. Pharm. Sci. 98 (2009) 3499-3508. An attractive strategy is sialylation in vitro of recombinantly produced proteins (such as but not limited to immunoglobulins and growth factors), particularly therapeutic proteins. To this end, several research groups described expression of sialyltransferases in transformed organisms and purification of the recombinantly produced sialyltransferases. As glycosyltransferases of prokaryotic origin usually do not act on complex glycoproteins (e.g. antibodies), sialyltransferases from mammalian origin were studied with preference.

Particular glycoproteins subject to the disclosures and all aspects of the present document and the aspects and embodiments herein comprise without limitation cell surface glycoproteins and glycoproteins present in soluble form in serum ("serum glycoprotein"), the glycoproteins particularly being of mammalian origin. A "cell surface glycoprotein" is understood to be glycoprotein of which a portion is located on and bound to the surface of a membrane, by way of a membrane anchor portion of the surface glycoprotein's polypeptide chain, wherein the membrane is part of a biological cell. The term cell surface glycoprotein also encompasses isolated forms of the cell surface glycoprotein as well as soluble fragments thereof which are separated from the membrane anchor portion, e.g. by proteolytic cleavage or by recombinant production of such soluble fragments. A "serum glycoprotein" is understood as a glycoprotein being present in serum, i.e. a blood protein present in the non-cellular portion of whole blood, e.g. in the supernatant following sedimentation of cellular blood components. Without limitation, a specifically regarded and embodied serum glycoprotein is an immunoglobulin. Particular immunoglobulins mentioned in here belong to the IgG group (characterized by Gamma heavy chains), specifically any of four the IgG subgroups. For the disclosures, aspects and embodiments herein the term "serum glycoprotein also encompasses a monoclonal antibody; monoclonal antibodies artificially are well known to the art and can be produced e.g. by hybridoma cells or recombinantly using transformed host cells. A further serum specific glycoprotein is a carrier protein such as serum albumin, a fetuin, or another glycoprotein member of the superfamily of histidine-rich glycoproteins of which the fetuins are members. Further, without limitation, a specifically regarded and embodied serum glycoprotein regarding all disclosures, aspects and embodiments herein is a glycosylated protein signaling molecule. A particular molecule of this group is erythropoietin (EPO).

For in vitro engineering of glycoproteins glycosyltransferases can be used as an efficient tool (Weijers 2008). Glycosyltransferases of mammalian origin are compatible with glycoproteins as substrates whereas bacterial glycosyltransferases usually modify simpler substrates like oligosaccharides. For this reason synthetic changes in the glycan moieties of glycoproteins are advantageously made using mammalian glycosyltransferases as tools of choice. However, for a large scale application of glycosyltransferases in glycoengineering availability of suitable enzymes in large (i.e. industrial) quantities is required. The invention described herein particularly provides two variants with truncation deletions. Both variants, Δ89 hST6Gal-I and Δ108 hST6Gal-I exhibit sialylating hST6Gal-I enzyme activity.

Each truncation variant described herein is given a "delta" (="Δ") designation indicating the number of the last amino acid position of the respective truncation deletion, counted from the N-Terminus of the wild-type hST6Gal-I polypeptide according to SEQ ID NO:1 Two different N-terminal truncation variants, Δ89 hST6Gal-I (amino acid sequence shown in SEQ ID NO:2), and Δ108 hST6Gal-I (amino acid sequence shown in SEQ ID NO:3) were studied in more detail.

Expression vectors were constructed for expression of Δ89 hST6Gal-I and Δ108 hST6Gal-I, particularly using expression systems with mammalian cells such as CHO cells and HEK cells. Vectors with expression constructs for the Δ108 truncation variant of hST6Gal-I were made and for the Δ89 truncation variant of hST6Gal-I. To facilitate purification of the recombinantly expressed enzymes, the truncation variant polypeptides encoded by the constructs optionally included a N-terminal His-tag.

Yet, another aspect as disclosed herein is a transformed host organism, wherein the host organism is transformed with an expression vector as disclosed herein. With particular advantage, Human Embryonic Kidney 293 (HEK) cells can be used to practice the teachings as disclosed in here. A particular advantage of these cells is that they are very suited targets for transfection followed by subsequent culture. Thus, HEK cells can be efficiently used to produce target proteins by way of recombinant expression and secretion. Nevertheless, HeLa, COS and Chinese Hamster Ovary (CHO) cells are well-known alternatives and are included herein as specific embodiments of all aspects as disclosed herein.

A further aspect and a specific embodiment of all other aspects as disclosed herein is a recombinantly produced variant mammalian glycosyltransferase selected from Δ89 hST6Gal-I and Δ108 hST6Gal-I. Specifically, the variant is produced in a transformed HEK cell.

Yet, another aspect as disclosed herein is a method to produce recombinantly a variant mammalian glycosyltransferase, the method comprising the step of expressing in a host organism transformed with an expression vector a nucleotide sequence encoding a variant mammalian glycosyltransferase as disclosed herein, wherein a polypeptide is formed, thereby producing variant mammalian glycosyltransferase.

One aspect of the present disclosure, is a variant mammalian glycosyltransferase being capable of catalyzing formation of the α2,6 glycosidic bond of a N-acetylneuraminyl-α2,6-β-D-galactosyl-1,4-N-acetyl-β-D-glucosamine moiety in a glycoprotein glycan, wherein the mammalian glycosyltransferase is a N-terminally truncated human β-galactoside-α-2,6-sialyltransferase I of SEQ ID NO:2 (Δ89 hST6Gal-I). The enzymatic activity of Δ89 hST6Gal-I permits sialylation of not only a single one of the possible acceptor sites on the target molecule, as exemplified herein in a non-limiting way with IgG1 and IgG4 as target molecules.

A further aspect of the present disclosure, is a variant mammalian glycosyltransferase being capable of catalyzing formation of the α2,6 glycosidic bond of a N-acetylneuraminyl-α2,6-β-D-galactosyl-1,4-N-acetyl-β-D-glucosamine moiety in a glycoprotein glycan, wherein the mammalian glycosyltransferase is a N-terminally truncated human β-galactoside-α-2,6-sialyltransferase I of SEQ ID NO:3 (Δ108 hST6Gal-I). In contrast to Δ89 hST6Gal-I or functional equivalents thereof interaction of Δ108 hST6Gal-I with a target molecule typically permits sialylation of only a single acceptor site.

N-terminally truncated variants of glycosyltransferases are advantageously used in vitro due to their lack of transmembrane domains. Thus, such variants are useful for catalyzing and performing glycosyltransferase reactions in solution.

Surprisingly, the truncation variant Δ108 of hST6Gal-I (i.e. a variant hST6Gal-I protein with a polypeptide lacking the amino acids at positions 1-108 which are present in the corresponding wild-type polypeptide) was found to be enzymatically active; that is to say the Δ108 truncation variant of hST6Gal-I is capable of catalyzing transfer of a Neu5Ac residue to the C6 hydroxyl group of a free galactosyl residue being part of terminal Galβ1,4GlcNAc in a glycan or an antenna of a glycan, thereby forming in the glycan a terminal sialic acid residue α2→6 linked to the galactosyl residue of the Galβ1,4GlcNAc moiety. Furthermore, the Δ108 truncation variant of hST6Gal-I is suitable for glycoengineering applications to synthetically change the composition of glycan moieties of glycoproteins. Moreover, the Δ108 truncation variant of hST6Gal-I is well suited for recombinant expression in different host organisms, thereby allowing production of this enzyme in high amounts and at reasonable cost.

In addition, the variant Δ108 hST6Gal-I alone even more surprisingly appears to be restricted concerning its sialylating activity; thus it is capable of catalyzing the addition of only a single sialyl residue to a terminal acceptor moiety (Galβ1,4GlcNAc) comprised in the antennal glycan portion of a target molecule selected from a glycoprotein and a glycolipid, wherein the terminal acceptor moiety is capable of being α2,6 sialylated. Since sialylation of more than one acceptor (target) moiety of a single target molecule has not been observed, the Δ108 hST6Gal-I can advantageously be used for specific mono-sialylation. To the knowledge of the inventors such an enzymatic characteristic so far is unique.

A first aspect of all embodiments as disclosed herein is therefore the use of N-terminally truncated human β-galactoside-α-2,6-sialyltransferase I of SEQ ID NO:3 (Δ108 hST6Gal-I) for specifically forming a mono-sialylated target molecule from a target molecule, wherein the target molecule is selected from a glycoprotein or a glycolipid, wherein the target molecule comprises a plurality of (=two or more) antennal target moieties having as terminal structure a β-D-galactosyl-1,4-N-acetyl-β-D-glucosamine moiety with a hydroxyl group at the C6 position in the galactosyl residue, wherein the mono-sialylated target molecule comprises a single sialylated terminal antennal target moiety, and wherein the sialylated terminal antennal target moiety comprises one N-acetylneuraminyl-α2,6-β-D-galactosyl-1,4-N-acetyl-β-D-glucosamine residue. A specific embodiment is a method for producing in vitro a sialylated target molecule with a single sialyl residue added to one antennal terminal structure of the target molecule, the method comprising the steps of (a) providing a composition comprising (i) the target molecule, the target molecule being selected from a glycoprotein and a glycolipid, the target molecule comprising a plurality of antennae, at least two of the antennae each having as terminal structure a β-D-galactosyl-1,4-N-acetyl-β-D-glucosamine moiety with a hydroxyl group at the C6 position in the galactosyl residue; (ii) N-terminally truncated human β-galactoside-α-2,6-sialyltransferase I of SEQ ID NO:3 (Δ108 hST6Gal-I); (iii) cytidine-5'-monophospho-N-acetylneuraminic acid, or a functional equivalent thereof, as donor compound for a sialyltransferase-catalyzed reaction; (b) incubating the composition of step (a) under conditions permitting glycosyltransferase enzymatic activity, thereby forming per target molecule a single terminal antennal N-acetylneuraminyl-α2,6-β-D-galactosyl-1,4-N-acetyl-β-D-glucosamine residue (=α2,6 sialylated terminal antennal residue); thereby producing in vitro the sialylated target molecule with a single sialyl residue added to one antennal terminal structure of the target molecule.

In a specific embodiment of all aspects as disclosed herein the target molecule provided in step (a) is free of α2,6 sialylated terminal antennal residues. One way to arrive at such a target molecule is to remove any terminal sialyl residues with an enzyme having glycosidase, and specifically sialidase activity. This, using the above method with such an "asioalo" target protein which however retains its two or more acceptor sites for sialylation, the present disclosure, particularly the above use and method enables the skilled person to prepare specifically a mono-sialylated target molecule selected from a glycoprotein and a glycolipid, the mono-sialylated target molecule being obtainable by a method as disclosed in here.

The combination of Δ108 hST6Gal-I with an enzyme with unrestricted human β-galactoside-α-2,6-sialyltransferase I activity, such as particularly Δ89 hST6Gal-I, simultaneous use of both enzyme variants is particularly advantageous as it can be used for further controlled in vitro sialylisation of target molecules with two or more accessible antennal acceptor moiety/moieties. Thus, it was found that while Δ89 hST6Gal-I is capable of catalyzing sialylation to form bi-sialylated target proteins (exemplified herein in a non-limiting way by human monoclonal IgG1 and IgG4), under the same conditions Δ108 hST6Gal-I was only capable of catalyzing sialylation to form mono-sialylated target proteins which prior to sialylation were free of sialyl residues as terminal antennal moieties. Thus, a further process for quantitatively controlled sialylation was conceived, wherein the amount of enzymatic activity of each of Δ89 hST6Gal-I and Δ108 hST6Gal-I is pre-determined.

Remarkably, the combination of the particular two enzymes Δ89 hST6Gal-I and Δ108 hST6Gal-I allows sialylating in a quantitatively controlled way, in that in vitro sialylated IgG target molecules with a controlled ratio of mono- and bi-sialylated IgG target molecules can be produced, as in a non-limiting way exemplified herein. Suitable targets also in this embodiment include asialoglycoproteins, i.e. glycoproteins free of terminal antennal sialyl residues, e.g. obtained as glycoproteins from which prior to in vitro sialylation terminal sialic acid residues have been removed from antennal glycans by the action of sialidase-exhibiting enzymes. An example therefor is a neuraminidase.

As a further aspect as disclosed in here, for applying a combination of enzymes with β-galactoside-α-2,6-sialyltransferase I activity, in a first step, a composition is formed, the composition comprising an aqueous buffer permitting glycosyltransferase enzymatic activity, the composition further comprising: (a) a glycosylated target molecule, the target molecule being selected from a glycoprotein and a glycolipid, the target molecule comprising a plurality of antennae, at least two of the antennae each having as terminal structure a β-D-galactosyl-1,4-N-acetyl-β-D-glucosamine moiety with a hydroxyl group at the C6 position in the galactosyl residue; (b) terminally truncated human β-galactoside-α-2,6-sialyltransferase I of SEQ ID NO:3 (Δ108 hST6Gal-I); (c) a soluble N-terminally truncated human β-galactoside-α-2,6-sialyltransferase I variant with a sialyltransferase enzymatic activity higher or equal to that of N-terminally truncated human β-galactoside-α-2,6-sialyltransferase I of SEQ ID NO:2 (Δ89 hST6Gal-I); (d) cytidine-5'-monophospho-N-acetylneuraminic acid, or a functional equivalent thereof, as donor compound for a sialyltransferase-catalyzed reaction. In a specific embodiment the component of (c) is N-terminally truncated human β-galactoside-α-2,6-sialyltransferase I of SEQ ID NO:2 (Δ89 hST6Gal-I).

It was found that by varying the ratio of the two glycosyltransferase enzymes the ratio of mono- and bi-sialylated IgG target molecules could be controlled. Thus, in a specific embodiment each of Δ89 hST6Gal-I and Δ108 hST6Gal-I is present in a pre-determined amount. In another specific embodiment each amount of Δ89 hST6Gal-I and Δ108 hST6Gal-I has a pre-determined enzymatic activity. That is to say, with respect to each of the two enzymes the absolute amount of enzymatic activity in the composition is a measured amount which ultimately determines to which extent a mono-sialylated target molecule versus a bi- or even higher sialylated target molecule will be formed. Thus, reproducible ratios of mono- and bi- or higher sialylated target molecules became possible to produce.

Therefore, a further aspect as disclosed herein is the use of a composition as disclosed herein for producing in vitro and under conditions permitting glycosyltransferase enzymatic activity a sialylated target molecule having one or more sialyl residue(s) added to one or more antennal terminal structure(s) of the target molecule. In a specific embodiment, sialylation is determined quantitatively such that mono-sialylated target molecules on the one hand, and bi- or higher sialylated target molecules on the other hand are produced by way of simultaneously applying the enzymatic activities to the target molecule. It is reiterated here that as in each other aspect as disclosed herein an asialo target molecule is a specific embodiment with particular advantage for the practitioner of the present disclosure.

A further aspect of the present disclosure is a method for producing in vitro a sialylated target molecule with a controlled quantity of sialyl residues added to one or more antennal terminal structure(s) of the target molecule, the target molecule being selected from a glycoprotein and a glycolipid, the target molecule comprising a plurality of antennae, at least two of the antennae each having as terminal structure a β-D-galactosyl-1,4-N-acetyl-β-D-glucosamine moiety with a hydroxyl group at the C6 position in the galactosyl residue, the method comprising the steps of (a) providing a composition as disclosed herein, the composition comprising measured amounts of Δ108 hST6Gal-I and Δ89 hST6Gal-I or a soluble N-terminally truncated human β-galactoside-α-2,6-sialyltransferase I variant with a sialyltransferase enzymatic activity higher or equal to that of Δ89 hST6Gal-I, and/or measured enzymatic activities of Δ89 hST6Gal-I or the functional equivalent thereof and Δ108 hST6Gal-I; (b) incubating the composition of step (a) under conditions permitting glycosyltransferase enzymatic activity and for a pre-determined time interval, thereby forming terminal antennal N-acetylneuraminyl-α2,6-β-D-galactosyl-1,4-N-acetyl-β-D-glucosamine residue(s) [=α2,6 sialylated terminal antennal residue(s)], wherein Δ89 hST6Gal-I catalyzes formation of bi-sialylated IgG and Δ108 hST6Gal-I catalyzes formation of mono-sialylated IgG; thereby producing in vitro the sialylated target molecule with a controlled quantity of sialyl residues added to one or more antennal terminal structure(s) of the target molecule.

In a specific embodiment of all aspects as disclosed herein, the target molecule is selected from a glycolipid and a glycoprotein. A particular embodiment of a glycoprotein is selected from the group consisting of a cell surface glycoprotein, a glycosylated protein signaling molecule, a glycosylated immunoglobulin, and a glycosylated protein of viral origin. In a specific embodiment, the glycosylated immunoglobulin is selected from the group consisting of IgG1, IgG2, IgG3, IgG4. In a yet more specific embodiment, the glycosylated immunoglobulin is a monoclonal antibody.

In a specific embodiment of all aspects as disclosed herein, the target molecule is a glycoprotein and specifically a glycosylated protein signaling molecule, a glycosylated immunoglobulin, and a glycosylated protein of viral origin. The combined Δ89 and Δ108 hST6Gal-I variants were active in sialylation experiments using a recombinantly produced human monoclonal IgG4 antibody as a complex target (substrate) as one out of several non-limiting examples; similar findings were obtained using as a sialylation target a human IgG1 monoclonal antibody.

Apparently, the IgG-Fc glycan G2 has two galactose moieties at the termini of the antennate branches which can be sialylated. Under suitable reaction conditions, the N-terminally truncated variant Δ89 hST6Gal-I preferably catalyzes the synthesis of disialylated glycans (G2+2SA). At the same time and under the same conditions, the Δ108 hST6Gal-I catalyzes formation of only mono-sialylated (G2+1SA) glycans. And therefore, by way of combining the two enzymes in measured amounts it becomes possible to specifically synthesize mono- and bi-sialylated glycans at a pre-determined ratio.

Controlled sialylation as provided by the present disclosure is a novel means to synthesize in vitro mono-, bi-, and higher sialylated glycoproteins with a desired degree of sialylation. Thus, though exemplified by showing the desired technical effects with IgG molecules, the uses according to the disclosures in here also allow to process other glycoproteins in a similar way, with the proviso that concerning glysosyltransferase activity, the glycoproteins comprise two or more terminal antennate β-D-galactosyl-1,4-N-acetyl-β-D-glucosamine moieties. The same reasoning applies in an analogous way to glycolipids.

Recombinant humanized IgG1 and IgG4 monoclonal antibodies (mabs), characterized as G2+0SA, as well as EPO were used as targets in sialylation experiments (30 μg enzyme/300 μg target protein). Both enzyme variants of ST6Gal-I (delta89 and delta108) were used under identical reaction conditions and the G2+0SA, G2+1SA and G2+2SA status analyzed by mass spectrometry.

Due to the high expression rates and the efficient purification procedures both variants (delta89 and delta108) of recombinant human ST6-Gal-I are available in large quantities and with high purity. Both variants are active with high molecular weight substrates like monoclonal antibodies. They show different performance in sialylation experiments using monoclonal antibodies with bi-antennary glycan as substrate. Using the variant delta89 preferably bi-sialylated glycans are obtained, whereas under identical conditions using delta108 mono-sialylated glycans are obtained.

Tetra-antennary glycans are also accepted as substrate (data not shown). The results demonstrate that both variants can be successfully used for in vitro glycoengineering of therapeutic antibodies.

Recombinant human ST6-Gal-I is the first enzyme available in large quantities. Together with the already available donor substrates (activated sugars used as co-substrates), a highly advantageous set of reagents is provided for in vitro glycoengineering of proteins.

By practicing teachings as provided herein, recombinant Δ89 variant of human ST6-Gal-I is an enzyme available in large quantities. Together with the already available donor substrates (activated sugars used as co-substrates), a highly advantageous set of reagents is provided for quantitatively controlled in vitro glycoengineering of proteins.

The following items further provide specific aspects of the disclosure, and specific embodiments to practice the teachings provided herein.

1. A composition comprising an aqueous buffer permitting glycosyltransferase enzymatic activity, the composition further comprising:
   (a) a glycosylated target molecule, the target molecule being selected from a glycoprotein and a glycolipid, the target molecule comprising a plurality of antennae, at least two of the antennae each having as terminal structure a β-D-galactosyl-1,4-N-acetyl-β-D-glucosamine moiety with a hydroxyl group at the C6 position in the galactosyl residue;
   (b) N-terminally truncated human β-galactoside-α-2,6-sialyltransferase I of SEQ ID NO:2 (Δ89 hST6Gal-I) or a soluble N-terminally truncated human β-galactoside-α-2,6-sialyltransferase I variant with a sialyltransferase enzymatic activity higher or equal to that of Δ89 hST6Gal-I;
   (c) N-terminally truncated human β-galactoside-α-2,6-sialyltransferase I of SEQ ID NO:3 (Δ108 hST6Gal-I);
   (d) cytidine-5'-monophospho-N-acetylneuraminic acid, or a functional equivalent thereof, as donor compound for a sialyltransferase-catalyzed reaction.
2. The composition according to item 1, the buffer comprising sodium acetate, Tris (=tris(hydroxymethyl)aminomethane), potassium phosphate, and NaCl.
3. The composition according to any of the items 1 and 2, wherein the pH of the buffer is 6.5.

4. The composition according to any of the items 1 to 3, wherein each of Δ89 hST6Gal-I and Δ108 hST6Gal-I is present in a pre-determined amount.

5. The composition according to item 4, wherein each amount of Δ89 hST6Gal-I and Δ108 hST6Gal-I has a pre-determined enzymatic activity.

6. Use of a composition according to any of the items 1 to 5 for producing in vitro and under conditions permitting glycosyltransferase enzymatic activity a sialylated target molecule having one or more sialyl residue(s) added to one or more antennal terminal structure(s) of the target molecule.

7. The use according to item 6, wherein in a sialylated target molecule each terminal antennal structure with an added sialyl residue is a N-acetylneuraminyl-α2,6-β-D-galactosyl-1,4-N-acetyl-β-D-glucosamine residue.

8. The use according to any of the items 6 and 7 of a composition according to item 4 or item 5 for producing in vitro a sialylated target molecule with a controlled quantity of sialyl residues added to one or more antennal terminal structure(s) of the target molecule.

9. The use according to any of the items 6 to 8 within a pre-determined time interval, specifically a time interval selected from 0.5 to 8 hours, more specifically a time interval selected from 0.5 h, 1 h, 2 h, 3 h, 4 h, 5 h, 6 h, 7 h, and 8 h.

10. The use according to any of the items 6 to 9, wherein Δ89 hST6Gal-I predominantly catalyzes formation of a bi- or higher sialylated target molecule, and Δ108 hST6Gal-I predominantly catalyzes formation of a mono-sialylated target molecule.

11. A method for producing in vitro a sialylated target molecule with a controlled quantity of sialyl residues added to one or more antennal terminal structure(s) of the target molecule, the target molecule being selected from a glycoprotein and a glycolipid, the target molecule comprising a plurality of antennae, at least two of the antennae each having as terminal structure a β-D-galactosyl-1,4-N-acetyl-β-D-glucosamine moiety with a hydroxyl group at the C6 position in the galactosyl residue, the method comprising the steps of
(a) providing a composition according to item 4 or item 5;
(b) incubating the composition of step (a) under conditions permitting glycosyltransferase enzymatic activity and for a pre-determined time interval, thereby forming terminal antennal N-acetylneuraminyl-α2,6-β-D-galactosyl-1,4-N-acetyl-β-D-glucosamine residue(s) [=α2,6 sialylated terminal antennal residue(s)], wherein Δ89 hST6Gal-I catalyzes formation of bi-sialylated target molecule and Δ108 hST6Gal-I catalyzes formation of mono-sialylated target molecule;
thereby producing in vitro the sialylated target molecule with a controlled quantity of sialyl residues added to one or more antennal terminal structure(s) of the target molecule.

12. The method according to item 11, wherein the target molecule is incubated with Δ89 hST6Gal-I and Δ108 hST6Gal-I simultaneously in the same vessel and under the same conditions.

13. The method according to item 12, wherein Δ89 hST6Gal-I predominantly catalyzes formation of a bi- or higher sialylated target molecule, and Δ108 predominantly hST6Gal-I catalyzes formation of a mono-sialylated target molecule.

14. The method according to item 13, wherein the ratio of the two values of (i) Δ89 hST6Gal-I enzymatic activity and (ii) Δ108 hST6Gal-I enzymatic activity determines the quantity of sialyl residues which in step (b) are added to one or more antennal terminal structure(s) of the target molecule.

15. The method according to any of the items 13 and 14, wherein a higher amount of Δ108 hST6Gal-I enzymatic activity relative to the amount of Δ89 hST6Gal-I enzymatic activity results in an increased likelihood of formation of a mono-sialylated target molecule compared to the likelihood of formation of a bi- or higher sialylated target molecule.

16. The method according to any of the items 11 to 15, wherein the target molecule is contains no sialyl residue as antennal terminal structure.

17. The method according to the items 11 to 16, wherein prior to step (a) the target molecule is pre-treated with an enzyme with sialidase enzymatic activity.

18. The method according to any of the items 11 to 17, wherein the target molecule is selected from a glycolipid and a glycoprotein, and specifically glycosylated cell surface protein, a glycosylated protein signaling molecule, a glycosylated immunoglobulin, and a glycosylated protein of viral origin.

19. The method according to item 18, wherein the glycosylated immunoglobulin is a monoclonal antibody of the IgG class, specifically selected from an IgG1, IgG2, IgG3 and an IgG4.

20. A preparation of glycosylated target molecules, the target molecules being immunoglobulin molecules of the IgG class, wherein the amounts of mono- and bi-sialylated target molecules in the preparation are controlled quantities, the preparation being obtained by a method according to any of the items 11 to 19.

21. Use of a preparation of glycosylated immunoglobulin molecules according to item 20 for preparing a pharmaceutical composition.

22. Use of N-terminally truncated human β-galactoside-α-2,6-sialyltransferase I of SEQ ID NO:3 (Δ108 hST6Gal-I) for specifically forming a predominantly mono-sialylated target molecule from a target molecule,
wherein the target molecule is selected from a glycoprotein or a glycolipid,
wherein the target molecule comprises a plurality of antennal target moieties having as terminal structure a β-D-galactosyl-1,4-N-acetyl-β-D-glucosamine moiety with a hydroxyl group at the C6 position in the galactosyl residue,
wherein the mono-sialylated target molecule comprises a single sialylated terminal antennal target moiety, and
wherein the sialylated terminal antennal target moiety comprises one N-acetylneuraminyl-α2,6-β-D-galactosyl-1,4-N-acetyl-β-D-glucosamine residue.

23. A method for producing in vitro a sialylated target molecule with predominantly a single sialyl residue added to one antennal terminal structure of the target molecule, the method comprising the steps of
(a) providing a composition comprising
  i. the target molecule, the target molecule being selected from a glycoprotein and a glycolipid, the target molecule comprising a plurality of antennae, at least two of the antennae each having as terminal structure a β-D-galactosyl-1,4-N-acetyl-β-D-glucosamine moiety with a hydroxyl group at the C6 position in the galactosyl residue;
  ii. N-terminally truncated human β-galactoside-α-2,6-sialyltransferase I of SEQ ID NO:3 (Δ108 hST6Gal-I);

iii. cytidine-5'-monophospho-N-acetylneuraminic acid, or a functional equivalent thereof, as donor compound for a sialyltransferase-catalyzed reaction;

(b) incubating the composition of step (a) under conditions permitting glycosyltransferase enzymatic activity, thereby forming per target molecule a single terminal antennal N-acetylneuraminyl-α2,6-β-D-galactosyl-1,4-N-acetyl-β-D-glucosamine residue (=α2,6 sialylated terminal antennal residue);

thereby producing in vitro the sialylated target molecule with a single sialyl residue added to one antennal terminal structure of the target molecule.

24. The method according to item 23, wherein the target molecule provided in step (a) is free of α2,6 sialylated terminal antennal residues.

25. A mono-sialylated target molecule selected from a glycoprotein and a glycolipid, the mono-sialylated target molecule being obtainable by a method according to item 24.

26. Use of a mono-sialylated target molecule according to item 25 for preparing a pharmaceutical composition.

The Examples that follow are illustrative of specific embodiments of the disclosure, and various uses thereof. They set forth for explanatory purposes only, and are not to be taken as limiting the disclosure.

Example 1

Test for Sialyltransferase Enzymatic Activity

Asialofetuin (desialylated fetuin, Roche Applied Science) was used as acceptor and CMP-9-fluoro-NANA (CMP-9-fluoresceinyl-NeuAc) was used as donor substrate (Brossmer, R. & Gross H. J. (1994) Meth. Enzymol. 247, 177-193). Enzymatic activity was determined by measuring the transfer of sialic acid from the donor compound to asialofetuin. The reaction mix (35 mM MES, pH 6.0, 0.035% Triton X-100, 0.07% BSA) contained 2.5 µg of enzyme sample, 5 µL asialofetuin (20 mg/ml) and 2 µL CMP-9-fluoro-NANA (1.0 mg/ml) in a total volume of 51 µL. The reaction mix was incubated at 37° C. for 30 minutes. The reaction was stopped by the addition of 10 µL of the inhibitor CTP (10 mM). The reaction mix was loaded onto a PD10 desalting column equilibrated with 0.1 M Tris/HCl, pH 8.5. Fetuin was eluted from the column using the equilibration buffer. The fractions size was 1 mL. The concentration of formed fetuin was determined using a fluorescence spectrophotometer. Excitation wave length was 490 nm, emission was measured at 520 nm. Enzymatic activity was expressed as RFU (relative fluorescence unit). 10 000 RFU/µg is equivalent to a specific activity of 0.0839 nmol/µg×min.

Example 2

SDS Gel Electrophoresis

Analytical SDS gel electrophoresis was carried out using NuPAGE gels (4-12%, Invitrogen). Samples (36 µl) were diluted with 12 µl NuPAGE LDS sample buffer (Invitrogen) and incubated for 2 min at 85° C. Aliquots, typically containing 5 µg protein were loaded on the gel. The gels were stained using SimplyBlue SafeStain (Invitrogen).

Example 3

N-Terminal Sequencing by Edman Degradation

The N-terminal sequences of expressed variants of human ST6Gal-I were analyzed by Edman degradation using reagents and devices obtained from Life Technologies. Preparation of the samples was done as described in the instruction manual of the ProSorb Sample Preparation cartridges (catalog number 401950) and the ProBlott Mini PK/10 membranes (catalog number 01194). For sequencing the Procise Protein Sequencing Platform was used.

Example 4

Mass Spectrometry

The molecular masses of variants of human ST6Gal-I expressed in HEK cells were analyzed in mass spectrometry. Therefore, the glycosylated and deglycosylated forms of human ST6Gal-I were prepared and analyzed using Micromass Q-Tof Ultima and Synapt G2 HDMS devices (Waters UK) and MassLynx V 4.1 software.

Example 5

Mass Spectrometry of Glycosylated Human ST6Gal-I Enzymes

For mass spectrometry measurement the samples were buffered in electrospray medium (20% acetonitrile+1% formic acid). The buffer exchange was performed with Illustra™ MicroSpin™ G-25 columns (GE-Healthcare). 20 µg sialyltransferase variant with a concentration of 1 mg/ml was applied to the pre-equilibrated column and eluated by centrifugation. The resulting eluate was analyzed by electrospray ionization mass spectrometry.

Example 6

Mass Spectrometry of Deglycosylated Human ST6Gal-I Enzymes

For deglycosylation samples of the sialyltransferase were denatured and reduced. To 100 µg sialyltransferase 45 µL denaturing buffer (6 M guanidinium hydrochloride) and 13 µL TCEP (0.1 mM, diluted in denaturing buffer) were added. Further the appropriate volume of ultrapure water was added, so that the overall concentration of guanidinium hydrochloride was about 4 M. After incubation of the sample for 1 hour at 37° C. the buffer was changed using a Bio-SpinR 6 Tris column (Bio Rad), which was pre-equilibrated with ultrapure water. The whole sample was applied onto the column and eluted by centrifugation. To the resulting eluate 5.5 µl of 0.1 U/µl solution of PNGase F was added and incubated at 37° C. over night. Afterwards the samples were adjusted to 30% ACN and 1% FA and analyzed by electrospray ionization mass spectrometry.

Example 7

Cloning of pM1MT Expression Constructs for Transient Gene Expression (TGE) in Mammalian Host Cells Two fragments of human ST6Gal-I were cloned for the transient eukaryotic expression using an Erythropoetin signal sequence (Epo) and a peptide spacer of two (AP) or four (APPR) amino acids. For the N-terminally truncated fragments Epo-AP-delta89 hST6Gal-I (SEQ ID NO:4) and Epo-APPR-delta108 hST6Gal-I (SEQ ID NO:6) codon-optimized cDNAs were synthesized. Instead of the natural leader sequences and the N-terminal protein sequences, both hST6Gal-I coding regions harbor Erythropoetin signal sequence plus AP and APPR linker sequences in order to ensure correct processing of the polypeptides by the secretion machinery of the host cell line. In addition, the expression cassettes feature SalI and BamHI sites for cloning into the multiple cloning site of the predigested pM1MT vector fragment (Roche Applied Science). Expression of the hST6Gal-I coding sequences is therefore under control of a human cytomegalovirus (CMV) immediate-early enhancer/promoter region, followed by an intron A for regulated expression and a BGH polyadenylation signal.

Expression of the above constructs in HEK cells, and secretion of the variant hST6Gal-I proteins into cell supernatant was performed as described in Example 8.

Example 8

Transformation HEK Cells and Transient Expression and Secretion

Transient gene expression (TGE) by transfection of plasmid DNA is a rapid strategy to produce proteins in mammalian cell culture. For high-level expression of recombinant human proteins a TGE platform based on a suspension-adapted human embryonic kidney (HEK) 293 cell line was used. Cells were cultured in shaker flasks at 37° C. under serum-free medium conditions. The cells were transfected at approx. 2×10$^6$ vc/ml with the pM1MT expression plasmids (0.5 to 1 mg/L cell culture) complexed by the 293-Free™ (Merck) transfection reagent according to the manufacturer's guidelines. Three hours post-transfection, valproic acid, a HDAC inhibitor, was added (final conc. 4 mM) in order to boost the expression (Backliwal et al. (2008), Nucleic Acids Research 36, e96). Each day, the culture was supplemented with 6% (v/v) of a soybean peptone hydrolysate-based feed. The culture supernatant was collected at day 7 post-transfection by centrifugation.

Example 9

Purification of Recombinant Human ST6Gal-I Variants from HEK Cells

From supernatants of HEK cell fermentations different variants of hST6Gal-I (Epo-AP-delta89 hST6Gal-I and Epo-APPR-delta108 hST6Gal-I) were purified using a simplified purification protocol. In a first step, 0.1 liter of culture supernatant was filtrated (0.2 μm), the solution was dialysed against buffer A (20 mM potassium phosphate, pH 6.5). The dialysate was loaded onto a S-Sepharose ff column (1.6 cm×2 cm) equilibrated with buffer A. After washing with 100 ml buffer A, the enzyme was eluted with a linear gradient of 10 ml buffer A and 10 ml of buffer A+200 mM NaCl, followed by a wash step using 48 ml of buffer A+200 mM NaCl. Fractions (4 ml) were analysed by an analytical SDS gel electrophoresis. Fractions containing the enzyme were pooled and dialyzed against buffer B (50 mM MES, pH 6.0). The dialyzed pool was loaded onto a Heparin Sepharose ff column (0.5 cm×5 cm) equilibrated with buffer B and eluted using buffer B+200 mM NaCl. Fractions (1 ml) containing the enzyme were pooled and dialyzed against buffer B. Protein concentrations were determined at 280 nm (E280 nm [10 mg/ml]=1.931 for delta89ST6Gal-I and 1.871 for delta108ST6Gal-I). Mass spectrometry analysis of the enzyme showed that the construct of Epo-AP-delta89 hST6Gal-I was expressed without the N-terminal amino acids AP. This surprising finding indicated an unusual cleavage of the expressed protein by the signal peptidase. For the construct Epo-APPR-delta108 hST6Gal-I the N-terminal sequence was confirmed as APPR indicating the expected cleavage of the EPO signal sequence by the signal peptidase. For the recombinant human delta108 hST6Gal-I from HEK cells a specific activity of >600 RFU/mg was determined. The variant delta89 hST6Gal-I showed an increased specific activity of >1100 RFU/mg.

FIG. 1 shows the results of a SDS-PAGE of purified recombinant hST6Gal-I variants from HEK cells.

Example 10

Sialylation of Humanized Monoclonal Antibody (MAB)

A highly galactosylated humanized monoclonal antibody MAB IgG4 (WO 2005/023872) was used in sialylation experiments. The reaction mixture contained MAB IgG4 (300 μg in 55 μl 35 mM sodium actetate/Tris buffer pH 7.0), the donor substrate CMP-NANA (150 μg in 50 μl water) and sialyltransferase (30 μg in 20 mM potassium phosphate, 0.1 M NaCl, pH 6.5). The samples were incubated at 37° C. for a defined time. To stop the reaction 100 μl denaturing buffer (6 M guanidine hydrochloride) and 30 μl TCEP (0.1 mM, diluted in denaturing buffer) were added to the samples and the samples were incubated at 37° C. for 1 h. The samples were buffered in electrospray-medium (20% ACN, 1% FA) using pre-equilibrated Illustra™ Nap5-Columns (GE-Healthcare). Samples were analyzed by electrospray ionization mass spectrometry and the content of G2+0SA, G2+1SA and G2+2SA N-glycans was determined. A Micromass Q-Tof Ultima and a Synapt G2 HDMS device (Waters UK) were used, the software used was MassLynx V 4.1. To determine the kinetics of the sialylation the reaction was incubated up to 8 h.

Figure 2:
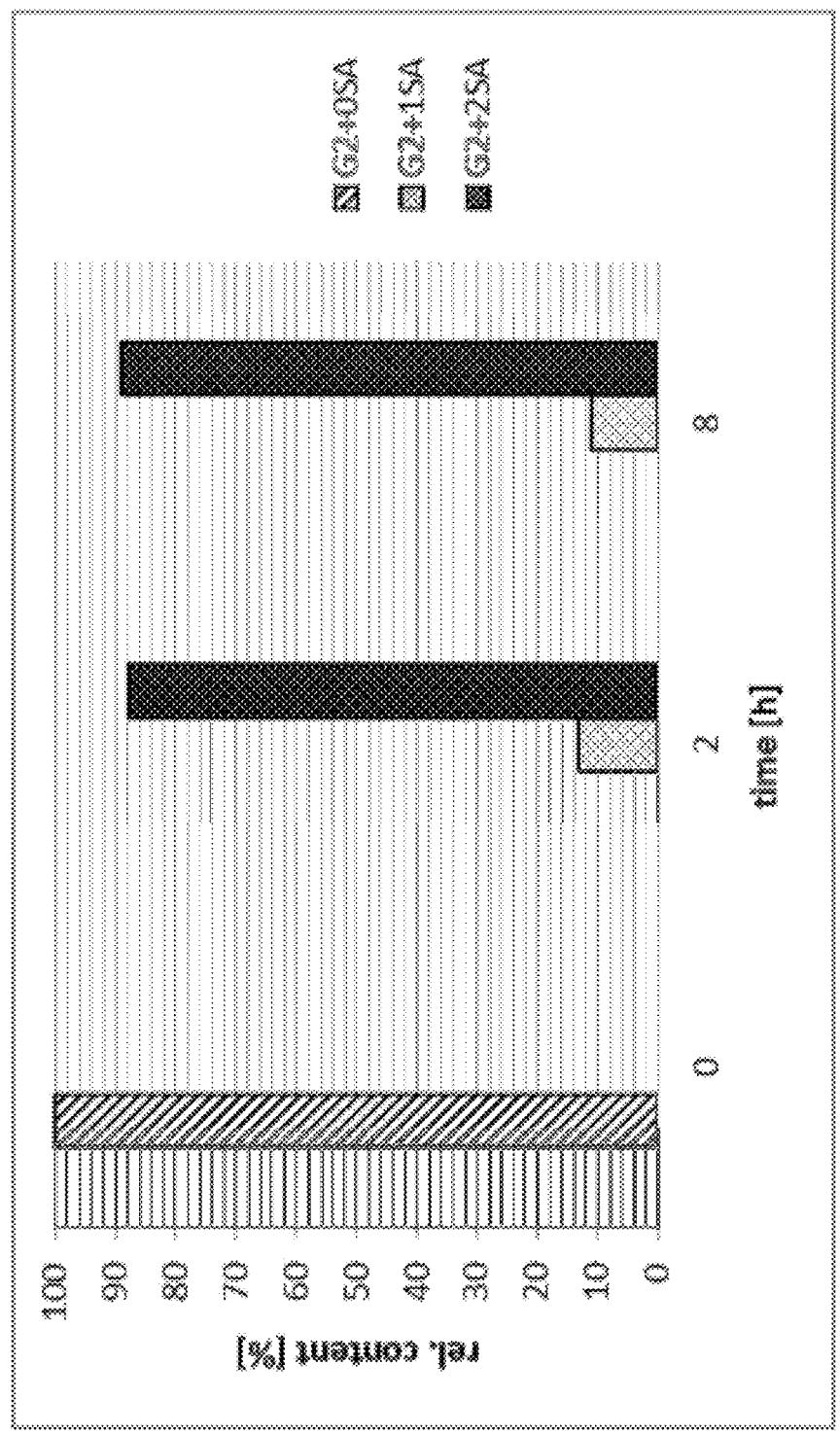
FIG. 2 Time course of sialylation of asialo MAB IgG4 using recombinant Δ89 hST6Gal-I. The relative content of glycan with terminal galactose residues (G2+0SA; "asialo"), mono-sialylated glycan (G2+1SA) and bi-sialylated glycan (G2+2SA) is shown.

The content of G2+0SA, G2+1SA and G2+2SA was determined by mass spectrometry. FIG. 2 shows the relative amounts of differently sialylated target proteins obtained after different time points during the incubation period with Δ89 hST6Gal-I. For the variant Δ89 hST6Gal-I already after 2 hours of incubation a high content (88%) of the bi-sialylated form G2+2SA was obtained, see FIG. 2. The data also show that the content of G2+2SA did not significantly increase after prolonged incubation for 8 h (89%).

Figure 3:
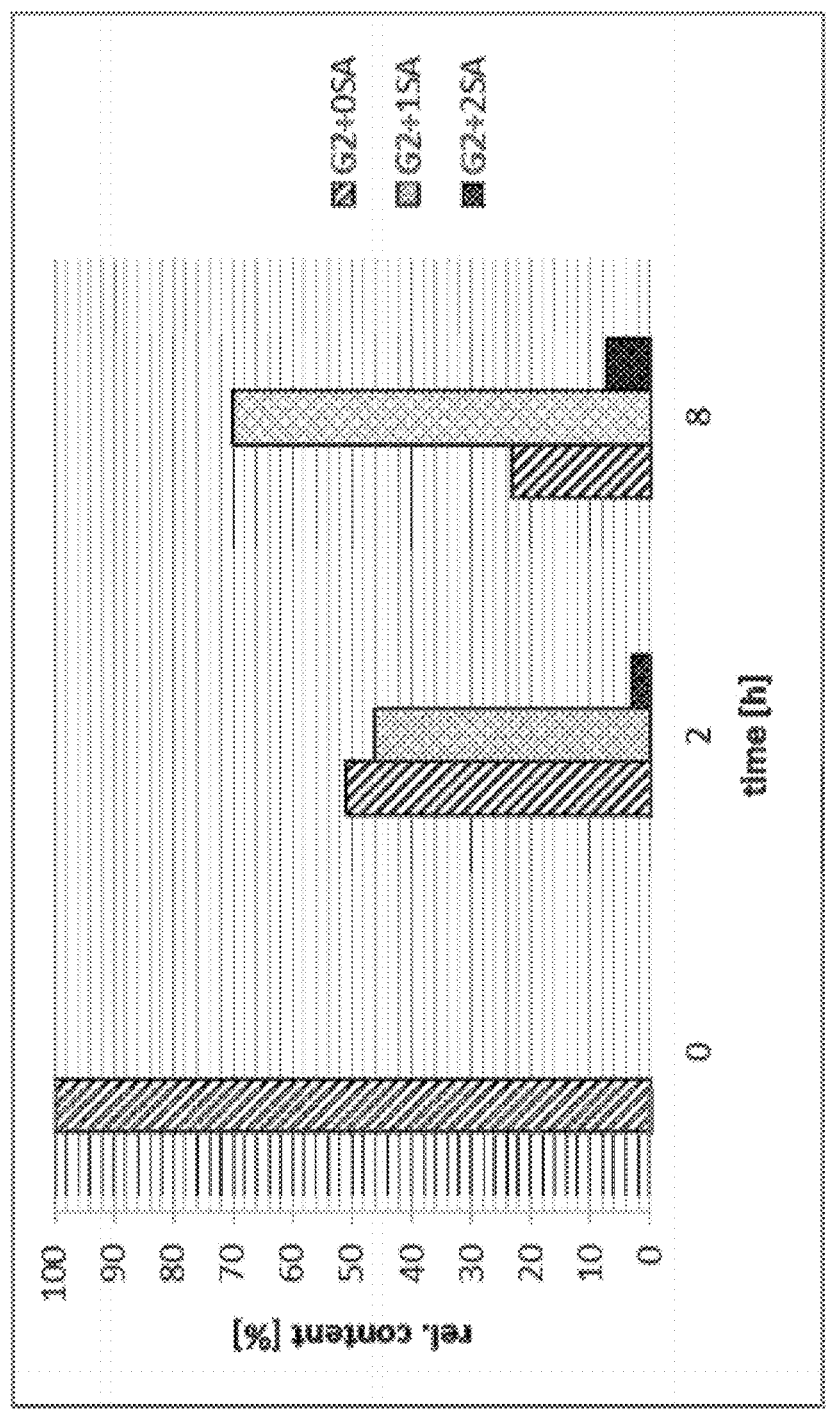
FIG. 3 Time course of sialylation of asialo MAB IgG4 using recombinant Δ108 hST6Gal-I. The relative content of glycan with terminal galactose residues (G2+0SA; "asialo"), mono-sialylated glycan (G2+1SA) and bi-sialylated glycan (G2+2SA) is shown.

In contrast, the variant delta108 hST6-Gal-I synthesized the monosialylated form G2+1SA. After 2 hours of incubation a content of 46% of the monosialylated form G2+1SA was obtained. After incubation for 8 h the content increased up to 70% G2+1SA (FIG. 3).

The invention claimed is:

1. A composition comprising an aqueous buffer permitting glycosyltransferase enzymatic activity, the composition further comprising:
   (a) a glycosylated target molecule, the target molecule being selected from a glycoprotein and a glycolipid, the target molecule comprising a plurality of antennae, at least two of the antennae each having as terminal structure a β-D-galactosyl-1,4-N-acetyl-β-D-glucosamine moiety with a hydroxyl group at the C6 position in the galactosyl residue;
   (b) N-terminally truncated human β-galactoside-α-2,6-sialyltransferase I of SEQ ID NO:2 (Δ89 hST6Gal-I);
   (c) N-terminally truncated human β-galactoside-α-2,6-sialyltransferase I of SEQ ID NO:3 (Δ108 hST6Gal-I); and
   (d) cytidine-5'-monophospho-N-acetylneuraminic acid as donor compound for a sialyltransferase-catalyzed reaction.

2. The composition according to claim 1, wherein the target molecule is a glycoprotein selected from the group consisting of a glycosylated cell surface protein, a glycosylated protein signaling molecule, a glycosylated immunoglobulin, and a glycosylated protein of viral origin.

3. The composition according to claim 1, wherein each of Δ89 hST6Gal-I and Δ108 hST6Gal-I is present in a predetermined amount.

4. The composition according to claim 3, wherein each amount of Δ89 hST6Gal-I and Δ108 hST6Gal-I has a pre-determined enzymatic activity.

5. A method for producing in vitro a sialylated target molecule with a controlled quantity of sialyl residues added to one or more antennal terminal structure(s) of the target molecule, the target molecule being selected from a glycoprotein and a glycolipid, the target molecule comprising a plurality of antennae, at least two of the antennae each having as terminal structure a β-D-galactosyl-1,4-N-acetyl-β-D-glucosamine moiety with a hydroxyl group at the C6 position in the galactosyl residue, the method comprising the steps of
   (a) providing the composition according to claim 3;
   (b) incubating the composition of step (a) under conditions permitting glycosyltransferase enzymatic activity and for a pre-determined time interval, thereby forming terminal antennal N-acetylneuraminyl-α2,6-β-D-galactosyl-1,4-N-acetyl-β-D-glucosamine residue(s), wherein Δ89 hST6Gal-I catalyzes formation of a bi-sialylated target molecule and Δ108 hST6Gal-I catalyzes formation of a mono-sialylated target molecule; thereby producing in vitro the sialylated target molecule with a controlled quantity of sialyl residues added to one or more antennal terminal structure(s) of the target molecule.

6. The method according to claim 5, wherein the target molecule is incubated with Δ89 hST6Gal-I and Δ108 hST6Gal-I simultaneously in the same vessel and under the same conditions.

7. The method according to claim 6, wherein Δ89 hST6Gal-I catalyzes formation of a bi- or higher sialylated target molecule, and Δ108 hST6Gal-I catalyzes formation of a mono-sialylated target molecule.

8. The method according to claim 7, wherein a higher amount of Δ108 hST6Gal-I enzymatic activity relative to the amount of Δ89 hST6Gal-I enzymatic activity results in an increased likelihood of formation of a mono-sialylated target molecule compared to the likelihood of formation of a bi- or higher sialylated target molecule.

9. The method according to claim 5, wherein the target molecule is contains no sialyl residue as antennal terminal structure.

10. The method according to claim 9, wherein the target molecule is a monoclonal antibody of the IgG class, specifically selected from the group consisting of IgG1, IgG2, IgG3 and an IgG4.

11. A method for producing in vitro a sialylated target molecule with a single sialyl residue added to one antennal terminal structure of the target molecule, the method comprising the steps of
   (a) providing a composition comprising
      i. the target molecule, the target molecule being selected from a glycoprotein and a glycolipid, the target molecule comprising a plurality of antennae, at least two of the antennae each having as terminal structure a β-D-galactosyl-1,4-N-acetyl-β-D-glucosamine moiety with a hydroxyl group at the C6 position in the galactosyl residue;
      ii. N-terminally truncated human β-galactoside-α-2,6-sialyltransferase I of SEQ ID NO:3 (Δ108 hST6Gal-I); and iii. cytidine-5'-monophospho-N-acetylneuraminic acid as donor compound for a sialyltransferase-catalyzed reaction;
(b) incubating the composition of step (a) under conditions permitting glycosyltransferase enzymatic activity, thereby forming per target molecule a single terminal antennal N-acetylneuraminyl-α2,6-β-D-galactosyl-1,4-N-acetyl-β-D-glucosamine residue;

thereby producing in vitro the sialylated target molecule with a single sialyl residue added to one antennal terminal structure of the target molecule.

12. The method according to claim 11, wherein the target molecule provided in step (a) is free of α2,6 sialylated terminal antennal residues.

\* \* \* \* \*